United States Patent
Gregolin et al.

(10) Patent No.: US 11,298,305 B2
(45) Date of Patent: *Apr. 12, 2022

(54) COMPOSITIONS AND METHODS FOR IMPROVING THE APPEARANCE OF THE HAIR

(71) Applicant: L'OREAL, Paris (FR)

(72) Inventors: Marina Tavares Gregolin, Rio de Janeiro-RJ (BR); Ana Paula Leme De Magalhães, Rio de Janeiro-RJ (BR); Manon Chaumontet, Paris (FR); Sintia Aguiar Martins, Rio de Janeiro-RJ (BR); Arthur Olimpio De Cunto Carvalho, Rio de Janeiro-RJ (BR)

(73) Assignee: L'OREAL, Paris (FR)

( * ) Notice: Subject to any disclaimer, the term of this patent is extended or adjusted under 35 U.S.C. 154(b) by 36 days.

This patent is subject to a terminal disclaimer.

(21) Appl. No.: 16/313,702

(22) PCT Filed: Jun. 30, 2016

(86) PCT No.: PCT/BR2016/050151
§ 371 (c)(1),
(2) Date: Dec. 27, 2018

(87) PCT Pub. No.: WO2018/000059
PCT Pub. Date: Jan. 4, 2018

(65) Prior Publication Data
US 2019/0167552 A1    Jun. 6, 2019

(51) Int. Cl.
| | |
|---|---|
| *A61K 8/42* | (2006.01) |
| *A61K 8/34* | (2006.01) |
| *A61Q 5/04* | (2006.01) |
| *A61K 8/898* | (2006.01) |

(52) U.S. Cl.
CPC ............. *A61K 8/42* (2013.01); *A61K 8/34* (2013.01); *A61K 8/345* (2013.01); *A61K 8/898* (2013.01); *A61Q 5/04* (2013.01); *A61K 2800/48* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 3,654,936 A | 4/1972 | Wajaroff | |
| 4,131,576 A | 12/1978 | Iovine et al. | |
| 5,635,170 A * | 6/1997 | Lang ............... | A61K 8/64 132/210 |
| 8,765,107 B2 | 7/2014 | Philippe et al. | |
| 2005/0102768 A1* | 5/2005 | Bartolone ............ | A61Q 5/10 8/401 |
| 2008/0025939 A1 | 1/2008 | Cassier et al. | |
| 2010/0028280 A1 | 2/2010 | Philippe et al. | |

FOREIGN PATENT DOCUMENTS

| | | |
|---|---|---|
| EP | 0095238 A2 | 11/1983 |
| EP | 1880706 A1 | 1/2008 |
| EP | 1880707 A1 | 1/2008 |
| EP | 1880708 A1 | 1/2008 |
| EP | 1880709 A1 | 1/2008 |
| EP | 1880710 A1 | 1/2008 |
| FR | 3004934 A1 | 10/2014 |
| JP | 2009-132625 A | 6/2009 |
| JP | 2010-070526 A | 4/2010 |
| JP | 2014-177438 A | 9/2014 |
| JP | 2016-017069 A | 2/2016 |
| JP | 2016-113384 A | 6/2016 |
| RU | 2007995 C1 | 2/1994 |
| WO | 2007/135297 A2 | 11/2007 |
| WO | 2012/027369 A2 | 3/2012 |
| WO | 2012/099110 A1 | 7/2012 |
| WO | 2013/098332 A2 | 7/2013 |
| WO | 2017/109067 A1 | 6/2017 |

OTHER PUBLICATIONS

Pal et al., Materials Chemistry and Physics 114: 530-532, 2009.*
International Search Report for counterpart Application No. PCT/EP2016/082371, dated Feb. 27, 2017.
Japanese Office Action for counterpart Application No. 2018-533120, dated May 7, 2019, English Translation,.
International Preliminary Report on Patentability for counterpart Application No. PCT/BR2016/050151, dated Mar. 28, 2018.
Non-Final Office Action for co-pending U.S. Appl. No. 16/064,310, dated Jul. 25, 2019.
International Search Report for counterpart Application No. PCT/BR2016/050151, dated Oct. 19, 2016.
International Preliminary Report on Patentability for counterpart Application No. PCT/BR2016/050151, report completed Mar. 28, 2018.
Final Office Action for co-pending U.S. Appl. No. 16/064,310, dated Feb. 7, 2020.
Non-Final Office Action for copending U.S. Appl. No. 16/064,310, dated Mar. 31, 2021.
Final Office Action for copending U.S. Appl. No. 16/064,310, dated Nov. 10, 2021.

* cited by examiner

*Primary Examiner* — Bong-Sook Baek
(74) *Attorney, Agent, or Firm* — The Marbury Law Group, PLLC

(57) ABSTRACT

The disclosure relates to compositions and methods for treating keratin fibers. Compositions comprise part (A) comprising (a) at least one compound chosen from urea and urea derivatives; and part (B) comprising (b) at least one polyol compound. Methods comprise applying the composition to keratin fibers to provide long-lasting effects such as good curl definition and regularity, better movement and discipline, and/or good volume and frizz control. Kits comprising the composition are also disclosed.

15 Claims, 8 Drawing Sheets

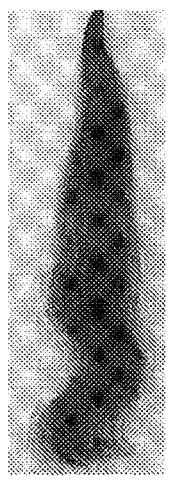
FIG. 2A　　　　FIG. 2B
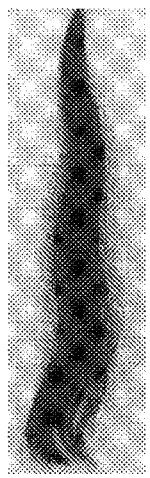
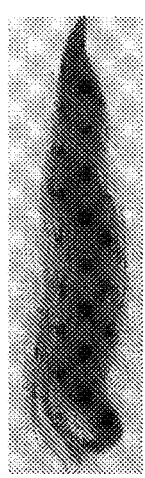
FIG. 3A　　　　FIG. 3B
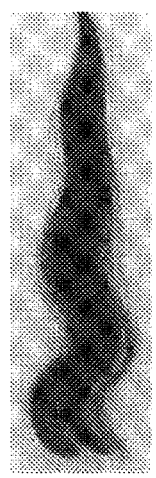
FIG. 4A　　　　FIG. 4B

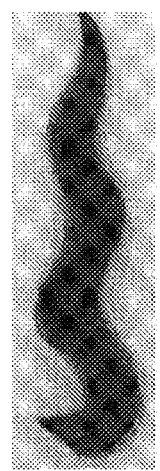 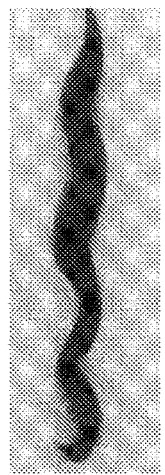
FIG. 5A    FIG. 5B
 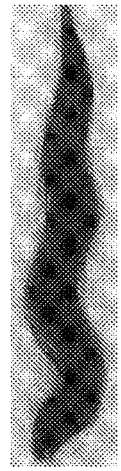
FIG. 6A    FIG. 6B
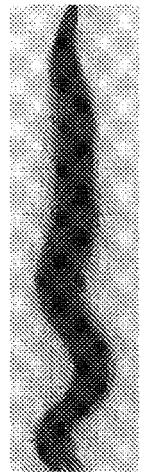 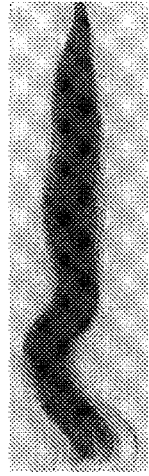
FIG. 7A    FIG. 7B

COMPOSITIONS AND METHODS FOR IMPROVING THE APPEARANCE OF THE HAIR

CROSS REFERENCE TO RELATED APPLICATION

This is a national stage application of PCT/BR2016/050151, filed internationally on Jun. 30, 2016, which is incorporated by reference herein in its entirety.

TECHNICAL FIELD

The disclosure relates to compositions and methods for improving the appearance of the hair.

BACKGROUND

Many people are dissatisfied with the appearance of their hair; in particular, people who have curly hair may wish to maintain the curls but gain better curl definition and regularity, better movement, and less volume and frizz. Additionally, some find it difficult to control, define, and/or style their curly hair.

Traditional processes for modifying curly hair include straightening or relaxing the hair. The processes for straightening or relaxing the hair generally involve reducing agents based on thiol or strong alkaline agents. These two techniques are based on cleavage of the disulfide covalent bonds present in keratin.

The first technique involves first opening the disulfide bonds using a composition comprising a reducing agent, optionally rinsing the hair, placing hair under tension, for example by using rollers, and subsequently reconstituting the disulfide bonds by applying to the hair an oxidizing composition also known as a "fixer" (fixing step), so as to give the head of hair the desired shape.

The second technique involves performing a lanthionization operation using a composition containing a base belonging to the hydroxide family. Unlike the first technique, this second technique does not require a fixing step because the formation of the lanthionine bonds is irreversible. Thus, this technique makes it possible, without preference, to perform waving, relaxing, uncurling or straightening of the hair. In particular, it is mainly used for relaxing naturally curly hair.

More recently, another technique has been developed which involves combining a heat treatment step and a step of applying a composition comprising formaldehyde. This technique is particularly effective for imparting a better appearance to damaged hair and/or for treating long hair and curly hair. When hair treated with formaldehyde is subjected to a high temperature, for example by means of an iron at 200° C. or higher, proteins of the keratin hair fibers crosslink by reaction of nucleophilic sites. However, the use of substances such as formaldehyde may prove to be irritating or even highly toxic.

These techniques have many drawbacks. In particular, they may lead to unpleasant odors during their use, a certain level of discomfort of the scalp, and/or substantial degradation of the keratin fibers. Moreover, these straightening or relaxing methods can lead to damage to the hair, including breakage, split ends, and slow growth. In addition, these methods can lead to straight, stiff hair with lack of movement.

Other treatments have been developed to loosen curls, rather than completely straighten curly hair. One such treatment involves moderating or controlling the effects of a traditional relaxer by modifying the processing conditions. For example oil can be added to a traditional relaxing solution, and the relaxer and oil can be rinsed from the hair before the end of the processing time. Another such modification includes treating the hair with oil before using a traditional relaxer, and rinsing the relaxer before the end of the processing time. These methods are difficult to control, and the resulting effect may be different textures of hair with little to no permissivity.

Treatment with a diluted relaxer has also been used to loosen curls, but this method can also damage hair, much like a traditional relaxer would.

As such, there is a consumer desire for methods for treating keratin fibers, in particular human keratin fibers such as curly hair, which make it possible to maintain curls while obtaining good curl definition and regularity, better movement, good volume and frizz control, and natural shape and result, and which are long-lasting, non-irritating, and non-toxic.

Furthermore, these methods may further provide care to keratin fibers and protection of keratin fibers against heat, in particular at the ends of the fibers.

SUMMARY

The disclosure relates to compositions and methods for treating keratin fibers, such as curly hair.

In one embodiment, the disclosure relates to compositions for treating keratin fibers such as curly hair, the compositions comprising:
a) at least one compound chosen from urea and urea derivatives, and
b) at least one polyol compound.

In further embodiments, the disclosure relates to methods for treating keratin fibers such as curly hair, the methods comprising:
1) applying to the keratin fibers a composition comprising:
a) at least one compound chosen from urea and urea derivatives, and
b) at least one polyol compound; and
2) heating the keratin fibers.

BRIEF DESCRIPTION OF THE DRAWINGS

The accompanying drawings, which are included to provide a further understanding of the invention and are incorporated in and constitute a part of this specification, together with the description serve to explain the principles of the invention.

FIGS. 2A-2B are photographs showing a lock of clean and dry hair before the treatment of Example II, with FIG. 2A showing the clean and dry lock, and FIG. 2B showing the clean and dry lock after ten shampoos.

FIGS. 3A-3B are photographs showing the lock of hair following treatment of Example 2, with FIG. 3A showing the lock after treatment of Example 2, and FIG. 3B showing the lock treated according to Example 2 after ten shampoos.

FIGS. 4A-4B are photographs showing the lock of hair following treatment of Example 3, with FIG. 4A showing the lock after treatment of Example 3, and FIG. 4B showing the lock treated according to Example 3 after ten shampoos.

FIGS. 5A-5B are photographs showing the lock of hair following treatment of Example 4, with FIG. 5A showing the lock after treatment of Example 4, and FIG. 5B showing the lock treated according to Example 4 after ten shampoos.

FIGS. 6A-6B are photographs showing the lock of hair following treatment of Example 5, with FIG. 6A showing the lock after treatment of Example 5, and FIG. 6B showing the lock treated according to Example 5 after ten shampoos.

FIGS. 7A-7B are photographs showing the lock of hair following treatment of Example 6, with FIG. 7A showing the lock after treatment of Example 6, and FIG. 7B showing the lock treated according to Example 6 after ten shampoos.

FIG. 10A is a photograph showing a lock of clean and dry hair before the treatment of Example 9. 10B-10C are photographs showing the lock of hair following treatment of Example 9, with FIG. 10B showing the lock after treatment of Example 9, and FIG. 10C showing the lock treated according to Example 9 after ten shampoos.

FIG. 12A is a photograph showing the head of clean and dry hair before the treatment of Examples 2 and 3. FIG. 12B is a photograph showing the head of hair following treatment of Examples 2 and 3. FIG. 12C is a photograph showing the heads of hair treated according to Examples 2 and 3 after three shampoos.

FIG. 13A is a photograph showing the head of clean and dry hair before the treatment of Examples 2 and 3. FIG. 13B is a photograph showing the head of hair following treatment of Examples 2 and 3. FIG. 13C is a photograph showing the heads of hair treated according to Examples 2 and 3 after three shampoos.

FIG. 14A is a photograph showing the head of clean and dry hair before the treatment of Example VI. FIG. 14B is a photograph showing the head of hair following treatment of Example VI.

FIG. 15A is a photograph showing the head of clean and dry hair before the treatment of Example I. FIG. 15B is a photograph showing the head of hair following treatment of Example I.

DETAILED DESCRIPTION

Figure 1A:
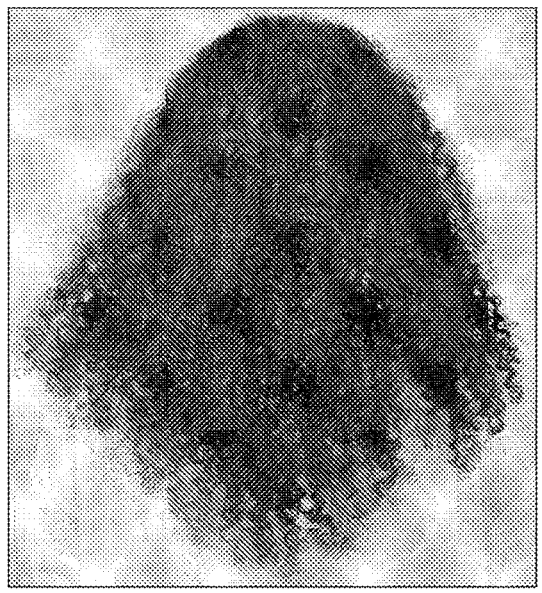
FIG. 1A is a photograph showing a head of clean and dry hair before the treatment of Example I.

In various embodiments, the disclosure relates to compositions and methods for treating keratin fibers. The compositions and methods may, in various embodiments, be effective at maintaining curly hair while obtaining one or more of good curl definition and regularity, long lasting curl definition and regularity, discipline, better movement, good volume and frizz control, and/or a natural shape and result.

Furthermore, certain embodiments feature treatments that are long-lasting, non-irritating, and non-toxic. In particular, some embodiments allow for long-lasting effects that can withstand several shampoo washes.

The composition and methods according to at least certain embodiments of the disclosure may also provide care to keratin fibers and protection of keratin fibers against heat, in particular at the ends of the keratin fibers. In some embodiments, the treated keratin fibers may be shiny, strong, and/or moisturized, and/or damage such as breakage, split ends, and slow growth, may be avoided.

As used herein, the term "long-lasting" means that the effects of the treatment last for at least about three shampoos, such as at least about 5 shampoos, at least about 6 shampoos, at least about 8 shampoos, at least about 10 shampoos, or at least about 15 shampoos, after the treatment.

As used herein, the term "lasting" it is meant to convey that the curl definition and regularity, good movement, and/or volume and frizz control remain substantially apparent.

As used herein, the term "lock" with regard to hair means a bunch of hair, either on a head of hair or apart from a head of hair, that is grouped together.

As used herein, the term "curl definition" with regard to hair means that the hair is separated into discrete locks of hair, wherein there is substantial uniformity in curl shape among each hair in a given lock such that the lock appears as an integral curl.

As used herein, the term "curl regularity" means that the hair is separated into discrete locks of hair, wherein there is substantial uniformity in curl shape among each lock of the hair such that the hair appears as an array of substantially similar curly locks.

As used herein, the term "volume control" means that the hair has low volume at the roots of the hair, and moderate volume along the length of the hair.

As used herein, the phrase "relative to the weight of the composition" with respect to the weight of a component is intended to indicate the total weight of the composition after any subformulations are mixed.

As used herein, the phrase "discipline" means that the hair is more manageable and less frizzy, and has fewer flyaways.

As used herein, "Hair Type" is used to describe the level of curl of the hair. Hair Type I is straight, Hair Type II is slightly wavy, Hair Type III is curly, Hair Type IV is highly curly, and Hair Type V is coily.

Composition

According to various embodiments, the composition comprises at least one compound chosen from urea and urea derivatives, at least one polyol compound, and optionally at least one solvent. Further optional components include at least one amino silicone, at least one thickener, and water.

In some embodiments, the composition comprises more than one subformulation. In particular, various embodiments of the composition comprise parts (A) and (B). Part (A) comprises (a) at least one compound chosen from urea and urea derivatives; and part (B) comprises (b) at least one polyol compound. Part (A) and/or part (B) may further optionally comprise (c) at least one solvent and/or (d) at least one amino silicone. According to various embodiments, water may be present in one or both of part (A) and part (B), and at least one thickener may be present in one or both of part (A) and part (B). If the composition comprises more than one subformulation, the subformulations may be combined and/or mixed prior to application onto the hair.

Urea and Urea Derivatives

The compositions according to various embodiments of the disclosure comprise at least one compound chosen from urea and urea derivatives. In embodiments having more than one subformulation, the at least one compound is chosen from urea and urea derivatives may be in part (A).

As used herein, the term "urea derivative" means any compound other than urea ($CO(NH_2)_2$) itself, comprising in its chemical formula a carbonyl group simply bonded to two nitrogen atoms, i.e. a unit represented by the chemical formula below:

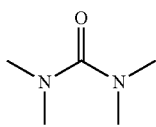

According to some embodiments, the urea or urea derivatives can denature certain proteins in the keratin fibers. The denaturing process slightly softens the keratin fibers in order to shape the fibers into a new shape or format.

In various embodiments, the at least one compound chosen from urea and urea derivatives are chosen from the compounds of formula (I) or (II), salts thereof, or hydrates thereof:

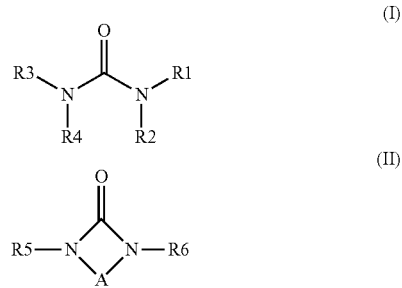

wherein in formulae (I) and (II):
R1, R2, R3, and R4, which may be identical or different, are chosen from a hydrogen atom; a linear or branched, cyclic or acyclic $C_1$-$C_5$ lower alkyl or alkenyl radical; a $C_1$-$C_5$ alkoxy radical; a $C_6$-$C_{18}$ aryl radical; or a 5- to 8-membered heterocyclic radical; these radicals being optionally substituted with a radical chosen from the following radicals: hydroxyl, ($C_1$-$C_4$)alkyl, (di)($C_1$-$C_4$)(alkyl)amino, dimethylamino, carboxyl, halogen, $C_6$-$C_{18}$ aryl, carboxamide, or N-methylcarboxamide;
it being understood that:
when R1, R2 and R3 represent a hydrogen atom, R4 may denote a radical chosen from: carboxamide, methoxy, ethoxy, 1,2,4-triazolyl, cyclopentyl, ($C_1$-$C_6$)alkylcarbonyl, acetyl, ($C_1$-$C_6$)alkoxycarbonyl, methoxycarbonyl, ethoxycarbonyl, CO—CH═CH—COOH, or phenyl optionally substituted with a chlorine atom or a hydroxyl, benzyl or 2,5-dioxo-4-imidazolidinyl radical;
when R1 and R3 represent a hydrogen atom, R2 may be chosen from a hydrogen atom or a methyl or ethyl radical, and R4 may represent an acetyl radical;
when R1 and R2 represent a hydrogen atom, R3 and R4 can form, together with the nitrogen atom that bears them, a 5- or 6-membered ring such as a piperidine, 3-methylpyrazole, 3,5-dimethylpyrazole, or maleimide ring;
R1 and R2 and also R3 and R4 can form, together with the nitrogen atom that bears them, an imidazole ring;
R5 and R6, which may be identical or different, are chosen from a hydrogen atom; a linear or branched, cyclic or acyclic $C_1$-$C_5$ lower alkyl, acyl or alkenyl radical; a $C_1$-$C_5$ alkoxy radical; a $C_6$-$C_{18}$ aryl radical; or a 5- to 8-membered heterocyclic radical; these radicals being optionally substituted with a radical chosen from the following radicals: hydroxyl, amino, dimethylamino, carboxyl, halogen, $C_6$-$C_{18}$ aryl, carboxamide, or N-methylcarboxamide; and
A is a radical chosen from the following radicals: $CH_2$—$CH_2$, CH═CH, $CH_2$—CO, CO—NH, CH═N, CO—CO, CHOH—CHOH, (HOOC)CH—CH, CHOH—CO, $CH_2$—$CH_2$—$CH_2$, $CH_2$—NH—CO, CH═C($CH_3$)—CO, NH—CO—NH, $CH_2$—$CH_2$—CO, $CH_2$—N($CH_3$)—$CH_2$, NH—$CH_2$—NH, CO—CH($CH_3$)—$CH_2$, CO—$CH_2$—CO, CO—NH—CO, CO—CH(COOH)—$CH_2$, CO—CH═C(COOH), CO—CH═C($CH_3$), CO—C($NH_2$)═CH, CO—C($CH_3$)═N, CO—CH═CH, CO—CH═N and CO—N═CH.

In some particular embodiments of the invention, the at least one compound chosen from urea and urea derivatives is of formula (I) and is chosen from:
urea
methylurea
ethylurea
propylurea
n-butylurea
sec-butylurea
isobutylurea
tert-butylurea
cyclopentylurea
ethoxyurea
hydroxyethylurea
N-(2-hydroxypropyl)urea
N-(3-hydroxypropyl)urea
N-(2-dimethylaminopropyl)urea
N-(3-dimethylaminopropyl)urea
1-(3-hydroxyphenyl)urea
benzylurea
N-carbamoylmaleamide
N-carbamoylmaleamic acid
piperidinecarboxamide
1,2,4-triazol-4-ylurea
hydantoic acid
methyl allophanate
ethyl allophanate
acetylurea
hydroxyethyleneurea
2-(hydroxyethyl)ethyleneurea
diallylurea
chloroethylurea
N,N-dimethylurea
N,N-diethylurea
N,N-dipropylurea
cyclopentyl-1-methylurea
1,3-dimethylurea
1,3-diethylurea
1,3-bis(2-hydroxyethyl)urea
1,3-bis(2-hydroxypropyl)urea 1,3-bis(3-hydroxypropyl)urea
1,3-dipropylurea
ethyl-3-propylurea
sec-butyl-3-methylurea
isobutyl-3-methylurea
cyclopentyl-3-methylurea
N-acetyl-N'-methylurea
trimethylurea
butyl-3,3-dimethylurea
tetramethylurea, or
a mixture of two or more of these compounds.

In other particular embodiments of the invention, the at least one compound chosen from urea and urea derivatives is of formula (II) and is chosen from:
parabanic acid
1,2-dihydro-3H-1,2,4-triazol-2-one
barbituric acid
uracil
1-methyluracil
3-methyluracil
5-methyluracil
1,3-dimethyluracil
5-azauracil
6-azauracil
5-fluorouracil
6-fluorouracil
1,3-dimethyl-5-fluorouracil
5-aminouracil
6-aminouracil
6-amino-1-methyluracil
6-amino-1,3-dimethyluracil
4-chlorouracil
5-chlorouracil
5,6-dihydrouracil
5,6-dihydro-5-methyluracil
2-imidazolidone
1-methyl-2-imidazolidinone
1,3-dimethyl-2-imidazolidinone
4,5-dihydroxyimidazolidin-2-one
1-(2-hydroxyethyl)-2-imidazolidinone
1-(2-hydroxypropyl)-2-imidazolidinone
1-(3-hydroxypropyl)-2-imidazolidinone
4,5-dihydroxy-1,3-dimethylimidazolidin-2-one
1,3-bis(2-hydroxyethyl)-2-imidazolidinone
2-imidazolidone-4-carboxylic acid
1-(2-aminoethyl)-2-imidazole
4-methyl-1,2,4-triazoline-3,5-dione
2,4-dihydroxy-6-methylpyrimidine
1-amino-4,5-dihydro-1H-tetrazol-5-one
hydantoin
1-methylhydantoin
5-methylhydantoin
5,5-dimethylhydantoin
5-ethylhydantoin
5-N-propylhydantoin
5-ethyl-5-methylhydantoin
5-hydroxy-5-methylhydantoin
5-hydroxymethylhydantoin
1-allylhydantoin
1-aminohydantoin
hydantoin-5-acetic acid
4-amino-1,2,4-triazolone-3,5-dione
hexahydro-1,2,4,5-tetrazine-3,6-dione
5-methyl-1,3,5-triazinon-2-one
1-methyltetrahydropyrimidin-2-one
2,4-dioxohexahydro-1,3,5-triazine
urazole
4-methylurazole
orotic acid
dihydroxyorotic acid
2,4,5-trihydroxypyrimidine
2-hydroxy-4-methylpyrimidine
4,5-diamino-2,6-dihydroxypyrimidine
1,3-dimethylbarbituric acid
cyanuric acid
1-methylhexahydropyrimidine-2,4-dione
1,3-dimethyl-3,4,5,6-tetrahydro-2-(1H)-pyrimidinone
5-(hydroxymethyl-2,4-(1H,3H)-pyrimidinedione
2,4-dihydroxypyrimidine-5-carboxylic acid
6-azathymine
5-methyl-1,3,5-triazinan-2-one
N-carbamoylmaleamic acid
alloxan monohydrate, or
a mixture of two or more of these compounds.

In certain embodiments, the at least one compound chosen from urea and urea derivatives is chosen from urea, hydroxyethylurea, or mixtures thereof.

The total amount of compound chosen from urea and urea derivatives ranges from about 1% to about 15% by weight, such as from about 2% to about 12% by weight, or from about 5% to about 10% by weight, relative to the total weight of the composition.

Polyol

The compositions according to various embodiments of the disclosure comprise at least one polyol. In embodiments having more than one subformulation, the at least one polyol may be in part (B).

As used herein, the term "polyol" means an organic compound comprising at least two hydroxyl groups (—OH), borne by different carbon atoms, this compound possibly being aliphatic, acyclic, linear or branched.

According to at least certain embodiments, the polyol acts as a propenetrating agent. As used herein, the term "propenetrating agent" means a compound that facilitates the penetration of actives with respect to the fiber.

In various embodiments, the at least one polyol that may be used according to embodiments of the disclosure comprises from about 2 to about 30 hydroxyl groups, such as from about 2 to about 10 hydroxyl groups, or from 2 to 3 hydroxyl groups.

According to certain embodiments, the at least one polyol comprises at least three carbon atoms.

In various embodiments, the at least one polyol is chosen from polyols comprising at least three carbon atoms and ethylene glycol, for example propylene glycol, butylene glycol, 1,3-propanediol (also called propanediol), 1,3-butylene glycol, 1,2-pentanediol, dipropylene glycol, hexylene glycol, pentylene glycol, glycerol, ethylene glycol, or mixtures thereof.

According to some embodiments, the at least one polyol is chosen from butylene glycol, 1,3-propanediol, propylene glycol, or mixtures thereof. In certain embodiments, the at least one polyol is chosen from butylene glycol. In yet certain other embodiments, the at least one polyol is chosen from 1,3-propanediol.

The total amount of polyol ranges from about 1% to about 30% by weight, such as from about 2% to about 15% by weight, or from about 8% to about 12% by weight, relative to the total weight of the composition.

According to certain embodiments, the weight ratio of the total amount of compound chosen from urea and urea derivatives, to the total amount of polyol, is greater than or equal to about 0.1, such as greater than or equal to about 0.2, or such as greater than or equal to about 0.3, or such as greater than or equal to about 0.4, or such as greater than or equal to about 0.5. In some embodiments, the weight ratio of the total amount of compound chosen from urea and urea derivatives, to the total amount of polyol, ranges from about 0.1 to about 1.5, such as from about 0.1 to about 1.1, such as from about 0.2 to about 1.1, such as from about 0.3 to about 1.1, such as from about 0.4 to about 1.1, such as from about 0.5 to about 1.1.

Amino Silicones

The compositions according to various embodiments of the disclosure may further comprise at least one amino silicone. In embodiments having more than one subformulation, the at least one amino silicone may be in part (A) and/or part (B).

As used herein, the term "amino silicone" means any silicone comprising at least one primary, secondary or tertiary amine function, or a quaternary ammonium group.

As used herein, the term "silicone" is intended to denote, in accordance with what is generally accepted, any organosilicon polymer or oligomer of linear or cyclic, branched or crosslinked structure, of variable molecular weight, obtained by polymerization and/or polycondensation of suitably functionalized silanes, and constituted essentially of a repetition of main units in which the silicon atoms are linked together via oxygen atoms (siloxane bond —Si—O—Si—), optionally substituted hydrocarbon-based groups being directly linked via a carbon atom to said silicon atoms. The hydrocarbon-based groups that are the most common are alkyl groups, especially of $C_1$-$C_{10}$, and in particular methyl, fluoroalkyl groups, the alkyl part of which is of $C_1$-$C_{10}$, and aryl groups and in particular phenyl.

According to various embodiments of the disclosure, compositions comprising at least one amino silicone may offer good cosmeticity.

In some embodiments, the at least one amino silicone comprises in its structure at least four silicon atoms.

The amino silicones of the composition that may be used in the composition according to various embodiments of the disclosure may be chosen from the silicones (a) to (f) below:

(a) the compounds corresponding to formula (III) below:

$$(R_1)_a(T)_{3-a}\text{-Si}[OSi(T)_2]_n\text{-}[OSi(T)_b(R_1)_{2-b}]_m\text{—}OSi(T)_{3-a}\text{-}(R_1)_a \quad (III)$$

wherein in formula (III):

T is chosen from a hydrogen atom or a phenyl, hydroxyl (—OH), $C_1$-$C_8$ alkyl, methyl, $C_1$-$C_8$ alkoxy, or methoxy group, in particular a methyl or methoxy group, a denotes the number 0 or an integer from 1 to about 3, and in particular 0, b denotes 0 or 1, and in particular 1, m and n are integers such that the sum (n+m) ranges from about 1 to about 2000, and in particular from about 50 to about 150, n possibly denoting a number from 0 to about 1999 and especially from about 49 to about 149, and m possibly denoting a number from about 1 to about 2000 and especially from about 1 to about 10, $R_1$ is a monovalent group of formula —$C_qH_{2q}$L in which q is an integer ranging from about 2 to about 8 inclusive, and L is an optionally quaternized amino group chosen from the following groups:

—N($R_2$)—$CH_2$—$CH_2$—N($R_2$)$_2$,
—N($R_2$)$_2$,
—$N^+$($R_2$)$_3$$Q^-$,
—$N^+$($R_2$)(H)$_2$$Q^-$,
—$N^+$($R_2$)$_2$H$Q^-$,
—N($R_2$)—$CH_2$—$CH_2$—$N^+$($R_2$)(H)$_2$$Q^-$, in which $R_2$ is chosen from a hydrogen atom, a phenyl group, a benzyl group, or a saturated monovalent hydrocarbon-based group, for example a $C_1$-$C_{20}$ alkyl group, and $Q^-$ represents an anionic counterion such as a halide ion, for instance fluoride, chloride, bromide, or iodide.

In particular, the amino silicones corresponding to the definition of formula (III) are chosen from the compounds corresponding to formula (IV) below:

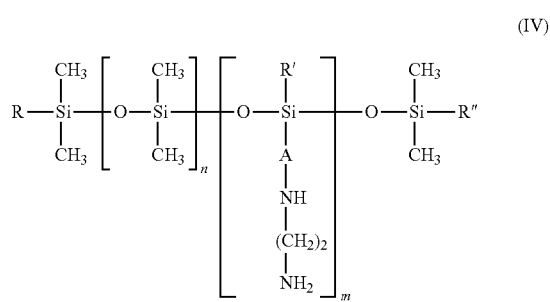

wherein in formula (IV):

R, R' and R", which may be identical or different, are chosen from a $C_1$-$C_4$ alkyl, methyl, $C_1$-$C_4$ alkoxy, methoxy, or hydroxyl group, in particular a methyl or methoxy group, A represents a linear or branched $C_3$-$C_8$ or $C_3$-$C_6$ alkylene group, in particular a $C_3$-$C_6$ alkylene group, m and n are integers that are dependent on the molecular weight and whose sum ranges from about 1 to about 2000 inclusive.

According to a particular embodiment of the disclosure, the at least one amino silicone is of formula (IV) wherein R, R' and R", which may be identical or different, each represent a $C_1$-$C_4$ alkyl or hydroxyl group, A represents a $C_3$ alkylene group, and m and n are such that the weight-average molecular mass of the compound ranges from about 5000 to about 500,000 g/mol inclusive. The compounds of this type are named "amodimethicone" in the CTFA dictionary.

According to another exemplary embodiment of the disclosure, the at least one amino silicone is of formula (IV) wherein R, R' and R", which may be identical or different, each represent a $C_1$-$C_4$ alkoxy or hydroxyl group, at least one of the groups R or R" is an alkoxy group, and A represents a $C_3$ alkylene group. The hydroxyl/alkoxy mole ratio may range from about 0.2:1 to about 0.4:1 inclusive, and in particular may be about 0.3:1.

In some embodiments, m and n are such that the weight-average molecular mass of the compound ranges from about 2000 to about $10^6$ inclusive. More particularly, n ranges from about 0 to about 999 and m ranges from about 1 to about 1000 inclusive, the sum of n and m ranging from about 1 to about 1000 inclusive.

In this category of compounds, mention may be made, inter alia, of the product Belsil® ADM 652 sold by the company Wacker.

According to another particular embodiment of the disclosure, the at least one amino silicone is of formula (IV) in which R and R", which are different, each represent a $C_1$-$C_4$ alkoxy or hydroxyl group, at least one of the groups R or R"

being an alkoxy group, R' representing a methyl group, and A representing a $C_3$ alkylene group. The hydroxyl/alkoxy mole ratio may range from about 1:0.8 to about 1:1.1 inclusive, for example may be about 1:0.95. Moreover, m and n are such that the weight-average molecular mass of the compound ranges from about 2000 to about 200,000 inclusive. More particularly, n ranges from about 0 to about 999 inclusive and m ranges from about 1 to about 1000 inclusive, the sum of n and m ranging from about 1 to about 1000.

Mention may be made of the product Fluid WR® 1300 sold by the company Wacker. Mention may also be made of the product Belsil® ADM Log 1 from Wacker.

Among the amino silicones of formula (IV), mention may also be made of the product Xiameter® MEM-8299 from Dow Corning.

It is noted that the molecular mass of these silicones may be determined by gel permeation chromatography (room temperature, polystyrene standard, μ styragem columns, eluent THF, flow rate of 1 mm/minute, 200 μl of a solution containing 0.5% by weight of silicone in THF are injected, and detection is performed by refractometry and UV-metry).

According to a particularly advantageous embodiment of the disclosure, the at least one amino silicone is of formula (III), and in particular the amino silicone of the composition that may be used in the process according to the invention is the polymer known in the CTFA dictionary as trimethylsilyl amodimethicone, corresponding to formula (V) below:

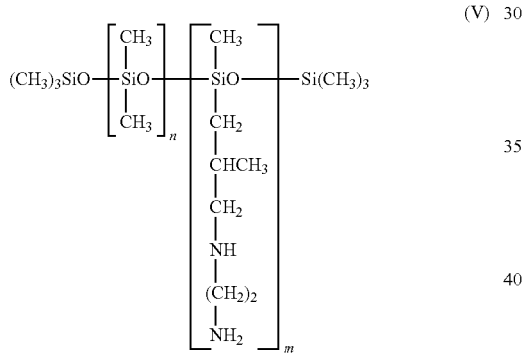

wherein in formula (V), m and n are integers that are dependent on the molecular weight and whose sum ranges from about 1 to about 2000 inclusive.

In certain embodiments, m and n are such that the weight-average molecular mass of the compound ranges from about 5000 to about 500,000 g/mol inclusive.

In some embodiments, m and n are such that the weight-average molecular mass of the compound ranges from about 2000 to about $10^6$ inclusive. More particularly, n ranges from about 0 to about 999 and m ranges from about 1 to about 1000 inclusive, the sum of n and m ranging from about 1 to about 1000 inclusive.

Moreover, m and n are such that the weight-average molecular mass of the compound ranges from about 2000 to about 200,000 inclusive. More particularly, n ranges from about 0 to about 999 inclusive and m ranges from about 1 to about 1000 inclusive, the sum of n and m ranging from about 1 to about 1000.

Such compounds are described, for example, in patent EP 0095238, incorporated by reference herein. A compound of formula (III) is sold, for example, under the name Q2-8220 by the company OSI;

(b) the compounds corresponding to formula (VI) below:

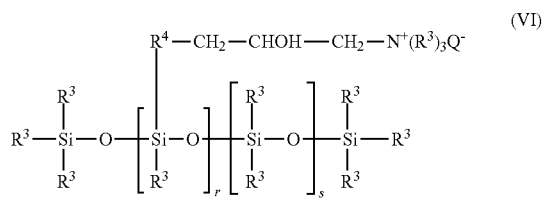

wherein in formula (VI):

$R^3$ represents a monovalent $C_1$-$C_{18}$ hydrocarbon-based group, and in particular a $C_1$-$C_{18}$ alkyl or $C_2$-$C_{18}$ alkenyl group, for example methyl;

$R^4$ represents a divalent hydrocarbon-based group, in particular a $C_1$-$C_{18}$ alkylene group or a divalent $C_1$-$C_{18}$, for example $C_1$-$C_8$, alkyleneoxy group;

$Q^-$ represents an anionic counterion chosen from halide ions, in particular chloride;

r represents a mean statistical value ranging from about 2 to about 20 inclusive, and in particular from about 2 to about 8;

s represents a mean statistical value ranging from about 20 to about 200 inclusive, and in particular from about 20 to about 50 inclusive;

(c) quaternary ammonium silicones, especially of formula (VII):

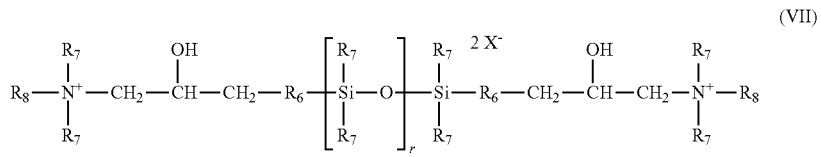

wherein in formula (VII):

$R_6$ represents a divalent hydrocarbon-based group, in particular a $C_1$-$C_{18}$ alkylene group or a divalent $C_1$-$C_{18}$, for example $C_1$-$C_8$, alkyleneoxy group linked to the Si atom via an SiC bond;

$R_7$, which may be identical or different, represent a monovalent hydrocarbon-based group containing from 1 to 18 carbon atoms, and in particular a $C_1$-$C_{18}$ alkyl group, a $C_2$-$C_{18}$ alkenyl group, or a ring comprising 5 or 6 carbon atoms, for example methyl;

$R_8$, which may be identical or different, are each chosen from a hydrogen atom, a monovalent hydrocarbon-based group containing from 1 to 18 carbon atoms, and in particular a $C_1$-$C_{18}$ alkyl group, a $C_2$-$C_{18}$ alkenyl group or a group —$R_6$—N(H)—C(O)—$R_7$, with $R_6$ and $R_7$ as defined previously;

$X^-$, which may be identical or different, represents an anionic counterion such as a halide ion, in particular chloride or an anionic counterion derived from an organic acid such as ($C_1$-$C_6$)alkylcarboxylate;

r represents a mean statistical value ranging from about 2 to about 200 inclusive and in particular ranging from about 5 to about 100;

(d) the amino silicones of formula (VIII):

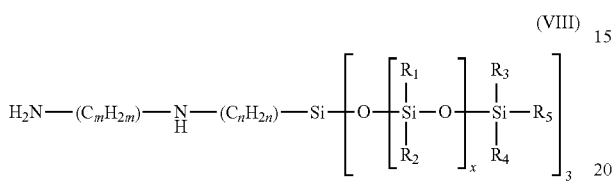

wherein in formula (VIII):

$R_1$, $R_2$, $R_3$ and $R_4$, which may be identical or different, are each chosen from a $C_1$-$C_4$ alkyl group, or an aryl group, in particular phenyl, $R_5$ is chosen from a $C_1$-$C_4$ alkyl group or a hydroxyl group, n and m, which may be identical or different, represent an integer ranging from about 1 to about 5 inclusive, and x is such that the amine number ranges from about 0.01 meq/g to about 1 meq/g;

(e) the amino silicones bearing polyalkoxylene groups of formula (IX):

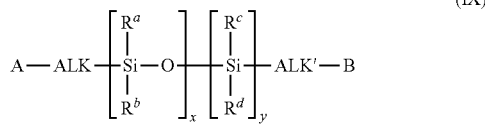

wherein in formula (IX):

$R^a$, $R^b$, $R^c$ and $R^d$, which may be identical or different, are each chosen from a hydroxyl group, or a linear or branched ($C_1$-$C_{10}$)alkyl group, in particular $R^a$, $R^b$, $R^c$ and $R^d$ each independently represent a ($C_1$-$C_6$)alkyl group, more particularly a linear group such as methyl;

ALK and ALK', which may be identical or different, represent a linear or branched ($C_1$-$C_{10}$)alkylene group, preferably a linear group such as propylene;

A and B, which may be identical or different, represent an aminopolyalkoxy group below:

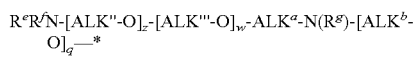

wherein:

* representing the point of attachment of the radical to the rest of the molecule via ALK or ALK';

$R^e$, $R^f$ and $R^g$, which may be identical or different, are each chosen from a hydrogen atom or a linear or branched ($C_1$-$C_{10}$)alkyl group, in particular $R^e$, $R^f$ and $R^g$ represent a hydrogen atom;

ALK" and ALK'", which may be identical or different, represent a linear or branched ($C_1$-$C_{10}$)alkylene and in particular $C_2$ or $C_3$ alkylene group; more particularly, ALK" represents a divalent group —$CH_2$—CH($CH_3$)— and ALK'" represents an ethylene group;

$ALK^a$ and $ALK^b$, which may be identical or different, represent a linear or branched ($C_1$-$C_{10}$)alkylene, in particular a $C_2$ or $C_3$, alkylene group, which is optionally substituted, for example with a hydroxyl group; more particularly, $ALK^a$ represents an ethylene or propylene group or a divalent group —$CH_2$—CH($CH_3$)— and $ALK^b$ represents a divalent group —$CH_2$—CH(OH)—$CH_2$—;

q, which may be identical or different, represent 0 or 1, in particular 1;

w, which may be identical or different, represent an integer, in particular the sum of the w values (w of A+w of B) having a mean value ranging from about 10 to about 100 inclusive, more particularly ranging from about 20 to about 60 inclusive, for example ranging from about 30 to about 50, such as 40-41;

z, which may be identical or different, represent an integer, in particular the sum of the z values (z of A+z of B) having a mean value ranging from about 1 to about 20 inclusive, more particularly ranging from about 1 to about 10 inclusive, for example ranging from about 2 to about 5, such as 3; and (f) amino silicones bearing polyalkoxylene groups constituted of polysiloxane blocks and of polyalkoxylene blocks comprising at least one amine group, in particular:

those of formula (X):

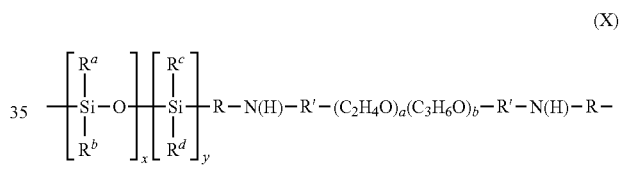

wherein in formula (X):

$R^a$, $R^b$, $R^c$ and $R^d$, which may be identical or different, are chosen from a hydroxyl group or a linear or branched ($C_1$-$C_{10}$) alkyl group, in particular $R^a$, $R^b$, $R^c$ and $R^d$ represent a ($C_1$-$C_4$)alkyl group, more particularly a linear group such as methyl;

R, which may be identical or different, represent a linear or branched $C_2$-$C_6$ alkylene radical, which is optionally hydroxylated and/or optionally interrupted with an oxygen atom;

a and b, which may be identical or different, represent a number ranging from about 0 to about 100;

R', which may be identical or different, is chosen from a hydrogen atom or a $C_1$-$C_4$ alkyl radical such as a methyl radical;

x denotes an integer ranging from about 1 to about 500 and y denotes an integer ranging from about 1 to about 10;

those containing units of formula (XI)

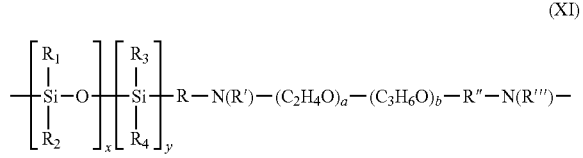

wherein in formula (XI):
R$_1$ to R$_4$, which may be identical or different, represent a C$_1$-C$_4$ alkyl radical, and in particular methyl;
R and R″, which may be identical or different, represent a linear or branched C$_2$-C$_6$ alkylene radical, which is optionally hydroxylated and/or optionally interrupted with an oxygen atom;
a and b, which may be identical or different, represent an integer ranging from about 0 to about 100;
R′ and R‴, which may be identical or different, are chosen from a hydrogen atom or a C$_1$-C$_4$ alkyl radical such as a methyl radical; and
x denotes a number ranging from about 1 to about 500 and y denotes a number ranging from about 1 to about 10;
those containing units of formula (XII) or of formula (XIII):

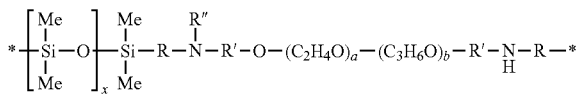
(XII)

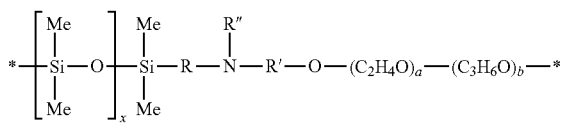
(XIII)

wherein in formulae (XII) and (XIII):
* represents the point of attachment;
Me represents a methyl group;
R, which may be identical or different, represent a linear or branched divalent C$_2$-C$_{12}$ alkyl radical, optionally comprising at least one heteroatom such as oxygen, in particular R, which may be identical or different, is chosen from an ethylene radical, a linear or branched propylene radical, a linear or branched butylene radical, or a radical —CH$_2$CH$_2$CH$_2$OCH(OH)CH$_2$—, in particular, R represents a radical —CH$_2$CH$_2$CH$_2$OCH(OH)CH$_2$—;
R′, which may be identical or different, represent a linear or branched divalent C$_2$-C$_{12}$ alkyl radical, optionally comprising at least one heteroatom such as oxygen, in particular R′, which may be identical or different, is chosen from an ethylene radical, a linear or branched propylene radical, a linear or branched butylene radical or a radical —CH$_2$CH$_2$CH$_2$OCH(OH)CH$_2$—, in particular, R′ represents a radical —CH(CH$_3$)—CH$_2$—;
R″ is chosen from a hydrogen atom or a methyl radical;
x denotes an integer ranging from about 1 to about 10,000, in particular ranging from about 10 to about 5000;
a represents an integer greater than or equal to 1, in particular ranging from about 5 to about 200, more particularly ranging from about 10 to about 100;
b represents an integer ranging from about 0 to about 200, in particular ranging from about 4 to about 100, more particularly ranging from about 5 to about 30.
In some embodiments, in the group of amino silicones (f), the polysiloxane block represents from about 50 mol % to about 95 mol %, in particular from about 70 mol % to about 85 mol %, relative to the total weight of the amino silicone.
According to various embodiments, in the group of amino silicones (f), the amine content ranges from about 0.02 meq. to about 0.5 meq., in particular from about 0.05 meq. to about 0.2 meq. per gram of copolymer in a dipropylene glycol solution containing 30% by weight of copolymer.

In certain embodiments, in the group of amino silicones (f), the weight-average molecular mass (Mw) of the amino silicone ranges from about 5000 g/mol to about 1,000,000 g/mol, for example from about 10,000 g/mol to about 200,000 g/mol.

As amino silicones (f), mention may be made especially of the silicones sold under the name Silsoft® A-843 or Silsoft® A+ by the company Momentive.

In some embodiments, the at least one amino silicone is chosen from the silicones of formulae (IV), (VIII), (XI), (XII) and (XIII).

Compositions according to certain embodiments of the disclosure comprise at least one amino silicone chosen from amodimethicone. In some embodiments, the at least one amino silicone is provided as an emulsion that further comprises surfactants chosen from nonionic or cationic surfactants, or mixtures thereof. Examples of such nonionic surfactants include, trideceth-5 and trideceth-10. An example of the cationic surfactant that may be present in the emulsion is cetrimonium chloride. In certain other embodiments, the compositions of the disclosure comprise at least one amino silicone chosen from amodimethicone which is provided as an emulsion that further comprises nonionic surfactants chosen from trideceth-5, trideceth-10, or mixtures thereof.

According to various embodiments of the disclosure, the total amount of the amino silicone represents from about 0.1% to about 4% by weight, such as from about 0.12% to about 3% by weight, or from about 0.13% to about 2% by weight, or from about 0.14% to about 1.5% by weight, relative to the total weight of the composition.

Thickeners

The compositions according to various embodiments of the disclosure optionally comprise at least one thickener. In embodiments having more than one subformulation, the optional thickener may be in part (A) and/or part (B).

As used herein, the term "thickener" means compounds which, by their presence, increase the viscosity of the composition into which they are introduced by at least 20 cps, such as by at least 50 cps, at 25° C. and at a shear rate of 1 s$^{-1}$. The viscosity may be measured using a cone/plate viscometer, a Haake R600 rheometer, or the like.

According to various embodiments, at least one thickener is employed to improve application of the composition and/or provide long lasting effects of the treatment. In certain embodiments, the at least one thickener has a synergistic effect with the solvent, for example to provide a long lasting effect of the treatment.

Suitable thickeners include nonionic, cationic, or amphoteric polymers and may be water-soluble or water-dispersible at a pH of 7 and at room temperature (25° C.).

As used herein, the terms "water-soluble" and "water-dispersible" refer to a polymer which forms in water at a weight concentration of 0.1% at pH 7 and at room temperature (25° C.) a visually homogeneous (one-phase) medium.

In various embodiments of the disclosure, the composition comprises at least one thickener chosen from saccharide-based thickeners.

As used herein, the term "saccharide-based" refers to a polymer constituted of units derived from a carbohydrate of formula C$_n$(H$_2$O)$_{n-1}$ or (CH$_2$O)$_n$, wherein n is a number ranging from about 3 to about 10 which may be optionally modified by substitution and/or by oxidation and/or by dehydration.

The units may especially be derived from the following carbohydrates: glucose, galactose, arabinose, rhamnose, mannose, xylose, fucose, anhydrogalactose, galacturonic acid, glucuronic acid, mannuronic acid, galactose sulfate, anhydrogalactose sulfate, fructose, or combinations thereof.

The saccharide-based thickeners that may be used according to exemplary embodiments of the disclosure may be chosen especially from nonionic or cationic associative saccharide-based thickening polymers and nonionic non-associative saccharide-based thickening polymers.

As used herein, the term "associative polymers" means polymers that are capable, in an aqueous medium, of reversibly combining with each other or with other molecules.

Associative polymers more particularly comprise at least one hydrophilic part and at least one hydrophobic part.

Thus, in particular, associative polymers comprise at least one hydrophobic group.

As used herein, the term "hydrophobic group" means a radical or polymer with a saturated or unsaturated, linear or branched hydrocarbon-based chain, comprising at least about 10 carbon atoms, in particular from about 10 to about 30 carbon atoms, in particular from about 12 to about 30 carbon atoms and more particularly from about 18 to about 30 carbon atoms.

According to some embodiments, the hydrocarbon-based chain is derived from a monofunctional compound.

By way of example, the hydrophobic group may be derived from a fatty alcohol such as stearyl alcohol, dodecyl alcohol, or decyl alcohol. It may also denote a hydrocarbon-based polymer, for instance polybutadiene.

The associative saccharide-based thickening polymers that may be used according to embodiments of the disclosure are especially chosen from:

(i) nonionic amphiphilic saccharide-based polymers comprising at least one fatty chain and at least one hydrophilic unit; or (ii) cationic amphiphilic saccharide-based polymers comprising at least one hydrophilic unit and at least one fatty-chain unit, the fatty chains containing from 10 to 30 carbon atoms.

The nonionic associative polymers are preferably chosen from:

(i) hydroxyethylcellulose, for instance the product NATROSOL 250 HHR PC or NATROSOL 250 HHR CS sold by the company Ashland;

(ii) celluloses modified with groups comprising at least one fatty chain; examples that may be mentioned include:
hydroxyethylcelluloses modified with groups comprising at least one fatty chain, such as alkyl, arylalkyl or alkylaryl groups, or mixtures thereof, and in which the alkyl groups are preferably $C_8$-$C_{22}$, for instance the product Natrosol® Plus Grade 330 CS ($C_{16}$ alkyls) sold by the company Ashland, or the product Bermocoll® EHM 100 sold by the companyAkzoNobel; methyl hydroxyethylcellulose; methyl ethyl hydroxyethylcellulose, known as the product STRUCTURE CEL 8000 M sold by the company AkzoNobel; or hydroxypropyl cellulose, known as the product KLUCEL MF PHARM HYDROXYPROPYLCELLULOSE sold by the company Ashland;
hydroxyethylcelluloses modified with alkylphenyl polyalkylene glycol ether groups, such as the product Amercell Polymer HM-1500 (nonylphenyl polyethylene glycol (15) ether) sold by the company Amerchol; or (iii) hydroxypropyl guars such as hydroxypropyl guar sold by as the product JAGUAR HP 105 by the company Rhodia and hydroxypropyl guars modified with groups comprising at least one fatty chain, such as the product Esaflor HM 22 ($C_{22}$ alkyl chain) sold by the company Lamberti, and the products RE210-18 ($C_{14}$ alkyl chain) and RE205-1 ($C_{20}$ alkyl chain) sold by the company Rhodia.

The cationic associative saccharide-based polymers are particularly chosen from quaternized cellulose derivatives.

In certain embodiments, the quaternized cellulose derivatives are, in particular:

(i) quaternized celluloses modified with groups comprising at least one fatty chain, such as linear or branched alkyl, linear or branched arylalkyl or linear or branched alkylaryl groups comprising at least 8 carbon atoms, or mixtures thereof;

(ii) quaternized hydroxyethylcelluloses modified with groups comprising at least one fatty chain, such as linear or branched alkyl, linear or branched arylalkyl or linear or branched alkylaryl groups comprising at least 8 carbon atoms, or mixtures thereof;

(iii) the hydroxyethylcelluloses of formula (XIV):

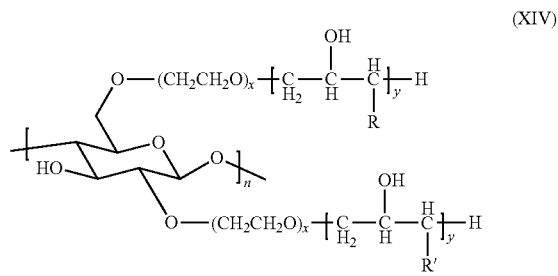

wherein in formula (XIV):

R and R', which may be identical or different, each represent an ammonium group such as $R_aR_bR_cN^+$—, $Q^-$, in which $R_a$, $R_b$ and $R_c$, which may be identical or different, are chosen from a hydrogen atom or a linear or branched $C_1$-$C_{30}$ and in particular a $C_1$-$C_{20}$ alkyl group, such as methyl or dodecyl;

$Q^-$ represents an anionic counterion such as a halide, for instance a chloride or bromide; and n, x and y, which may be identical or different, represent an integer ranging from about 1 to about 10,000.

The alkyl radicals borne by the above quaternized celluloses (i) or quaternized hydroxyethylcelluloses (ii) may comprise from about 8 to about 30 carbon atoms.

In some embodiments, the aryl radicals particularly denote phenyl, benzyl, naphthyl, or anthryl groups.

Examples of quaternized alkylhydroxyethylcelluloses containing $C_8$-$C_{30}$ fatty chains that may be indicated include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl), all sold by the company Amerchol, and the products Crodacel QM®, Crodacel QL® ($C_{12}$ alkyl) and Crodacel QS® ($C_{18}$ alkyl), all sold by the company Croda.

Mention may also be made of the hydroxyethylcelluloses of formula (XIV) in which R represents a trimethylammonium halide and R' represents a dimethyldodecylammonium halide, more preferentially R represents trimethylammonium chloride $(CH_3)_3N^+$ $Cl^-$ and R' represents dimethyldodecylammonium chloride $(CH_3)_2(C_{12}H_{25})N^+$ $Cl^-$. Polymers of this type are known under the trade name softCAT Polymer SL®, such as SL-100 and SL-60.

In some embodiments, the polymers of formula (XIV) have a viscosity ranging from about 2000 cPs to about 3000 cPs inclusive, such as from about 2700 cPs to about 2800 cPs inclusive.

According to certain embodiments, the saccharide-based thickeners are chosen from nonionic non-associative saccharide-based thickening polymers.

As nonionic non-associative saccharide-based thickening polymers that may be used according to embodiments of the disclosure, mention may be made more particularly of native gums such as:

1) tree or shrub exudates, in particular:
gum arabic (branched polymer of galactose, arabinose, rhamnose and glucuronic acid);
ghatti gum (polymer derived from arabinose, galactose, mannose, xylose and glucuronic acid);
karaya gum (polymer derived from galacturonic acid, galactose, rhamnose and glucuronic acid);
gum tragacanth (or tragacanth) (polymer of galacturonic acid, galactose, fucose, xylose and arabinose);

2) gums derived from algae, in particular:
agar (polymer derived from galactose and anhydrogalactose);
alginates (polymers of mannuronic acid and of glucuronic acid);
carrageenans and furcellerans (polymers of galactose sulfate and of anhydrogalactose sulfate);

3) gums derived from seeds or tubers, in particular:
guar gum (polymer of mannose and galactose);
locust bean gum (polymer of mannose and galactose);
fenugreek gum (polymer of mannose and galactose);
tamarind gum (polymer of galactose, xylose and glucose);
konjac gum (polymer of glucose and mannose);

4) microbial gums, including:
xanthan gum (polymer of glucose, mannose acetate, mannose/pyruvic acid and glucuronic acid);
gellan gum (polymer of partially acylated glucose, rhamnose and glucuronic acid);
scleroglucan gum (glucose polymer); or 5) plant extracts, in particular:
cellulose (glucose polymer);
starch (glucose polymer), and
inulin.

These nonionic non-associative saccharide-based thickening polymers may be physically or chemically modified.

As physical treatment, mention may especially be made of temperature treatment.

Chemical treatments that may be mentioned include esterification, etherification, amidation, or oxidation reactions.

These treatments can afford polymers that may especially be nonionic, anionic, or amphoteric.

In some embodiments, these chemical or physical treatments are applied to guar gums, locust bean gums, starches, and celluloses.

The nonionic guar gums that may be used according to embodiments of the disclosure may be modified with $C_1$-$C_6$ (poly)hydroxyalkyl groups.

Among the $C_1$-$C_6$ (poly)hydroxyalkyl groups, mention may be made, for example, of hydroxymethyl, hydroxyethyl, hydroxypropyl, and hydroxybutyl groups.

These modified guar gums may be prepared, for example, by reacting the corresponding alkene oxides, for instance propylene oxides, with native guar gum so as to obtain a guar gum modified with hydroxypropyl groups.

The degree of hydroxyalkylation in particular varies from about 0.4 to about 1.2 and corresponds to the number of alkylene oxide molecules consumed by the number of free hydroxyl functional groups present on the guar gum.

Such nonionic guar gums optionally modified with hydroxyalkyl groups are sold, for example, under the trade names Jaguar® HP8, Jaguar® HP60 and Jaguar® HP120, all by the company Rhodia Chimie.

The nonionic starches that may be used according to the invention may be chemically or physically modified especially by one or more of the following reactions: pregelatinization, oxidation, crosslinking, esterification, etherification, amidation, or heat treatments.

As modified starches that may be used according to the invention, mention may particularly be made of distarch phosphates or compounds rich in distarch phosphate, for instance the products sold under the references Prejel® VA-70-T AGGL (gelatinized hydroxypropyl cassava distarch phosphate), Prejel® TK1 (gelatinized cassava distarch phosphate) and Prejel® 200 (gelatinized acetyl cassava distarch phosphate), all by the company Avebe, or Structure Zea from National Starch (gelatinized corn distarch phosphate, also known as hydroxypropyl starch phosphate).

Mention may also be made of amphoteric starches, these amphoteric starches comprising at least one anionic groups and at least one cationic groups. The anionic and cationic groups may be linked to the same reactive site of the starch molecule or to different reactive sites; they are preferably linked to the same reactive site. The anionic groups may be of carboxylic, phosphate, or sulfate type, in particular carboxylic. The cationic groups can be of primary, secondary, tertiary, or quaternary amine type.

The native starch molecules used may originate botanically from cereals or tubers such as corn, potato, oat, rice, tapioca, sorghum, barley, wheat, cassava, or pea.

In certain embodiments, the starch is derived from potato.

It is also possible to use the hydrolysates of the starches mentioned above.

The celluloses that may be used according to the invention may be chemically or physically modified.

Modified celluloses that may be mentioned more particularly include cellulose polymers not comprising any $C_{10}$-$C_{30}$ fatty chains in their structure.

Thus, the cellulose polymers that may be used according to the invention may be chosen from unsubstituted celluloses, including those in a microcrystalline form, and cellulose ethers.

The modified celluloses that may be used according to embodiments of the disclosure may be cationic, amphoteric, or nonionic.

Among these cellulose-based polymers, mention may be made of cellulose ethers, cellulose esters, and cellulose ester ethers.

The cellulose ethers that may be used may more particularly be nonionic or cationic.

Among the nonionic cellulose ethers not bearing a $C_{10}$-$C_{30}$ fatty chain, i.e. "non-associative," mention may be made of ($C_1$-$C_4$)alkylcelluloses, such as methylcelluloses and ethylcelluloses (for example, Ethocel® standard 100 Premium from Dow Chemical); (poly)hydroxy($C_1$-$C_4$)alkylcelluloses, such as hydroxymethylcelluloses, hydroxyethylcelluloses (for example, Natrosol® 250 HHR provided by Aqualon) and hydroxypropylcelluloses (for example, Klucel® EF from Aqualon); mixed (poly)hydroxy($C_1$-$C_4$)alkyl-($C_1$-$C_4$) alkylcelluloses, such as hydroxypropylmethylcelluloses (for example, Methocel® E4M from Dow Chemical), hydroxyethylmethylcelluloses, hydroxyethylethylcelluloses (for example, Bermocoll® E 481 FQ from Akzo Nobel) and hydroxybutylmethylcelluloses.

Among the cationic cellulose ethers without a fatty chain, mention may be made of cationic cellulose derivatives such as cellulose copolymers or cellulose derivatives grafted with a water-soluble quaternary ammonium monomer, and described in particular in U.S. Pat. No. 4,131,576, such as (poly)hydroxy($C_1$-$C_4$)alkyl celluloses, for instance hydroxymethyl-, hydroxyethyl- or hydroxypropylcelluloses grafted especially with a methacryloylethyltrimethylammonium, methacrylamidopropyltrimethylammonium or dimethyldiallylammonium salt. The commercial products corresponding to this definition are more particularly the products sold under the names Celquat L 200® and Celquat H 100® by the company National Starch.

Among the cellulose esters are mineral esters of cellulose, such as cellulose nitrates, sulfates, phosphates, etc.; organic cellulose esters, such as cellulose monoacetates, triacetates, amidopropionates, acetatebutyrates, acetatepropionates and acetatetrimellitates, etc.; or mixed organic/mineral esters of cellulose, such as cellulose acetatebutyrate sulfates and cellulose acetatepropionate sulfates.

Among the cellulose ester ethers, mention may be made of hydroxypropylmethylcellulose phthalates and ethylcellulose sulfates.

The at least one thickener of the present invention may also be chosen from polymers such as the products sold under the name CARBOPOL (CTFA name: carbomer), homopolymers or copolymers of acrylic or methacrylic acids or the salts thereof and the esters thereof, such as the products sold under the names CARBOPOL ULTREZ 21 POLYMER (acrylates/C10-30 alkyl acrylate crosspolymer), commercially available from the company Lubrizol.

In other embodiments, the at least one thickener of the present invention may also be chosen from steareth-100/PEG-136/HDI copolymer, commercially available as the product RHEOLUXE 811 from the company Elementis.

According to various embodiments, the at least one thickener is chosen from hydroxyethylcellulose, steareth-100/PEG-136/HDI copolymer, hydroxypropylcellulose, methyl hydroxyethylcellulose, methyl ethyl hydroxyethylcellulose, acrylates/C10-30 alkyl acrylate crosspolymer, hydroxypropylguar, xanthan gum, hydroxypropyl starch phosphate, sodium polyacrylate, polyacrylate crosspolymer-6, or mixtures thereof.

In some embodiments, the at least one thickener is chosen from hydroxyethylcellulose, hydroxypropylcellulose, methyl ethyl hydroxyethylcellulose, acrylates/C10-30 alkyl acrylate crosspolymer, Steareth-100/PEG-136/HDI copolymer, and mixtures thereof.

The total amount of thickener may range from about 0.01% to about 10% by weight, such as from about 0.1% to about 5% by weight, or from about 0.5% to about 2.5% by weight, relative to the total weight of the composition.

Additional Components

The compositions according to various embodiments of the disclosure may optionally comprise at least one additional component chosen from surfactants, particularly chosen from nonionic, anionic, cationic and amphoteric surfactants; fixing polymers; conditioning agents, particularly chosen from cationic polymers; silicones other than the at least one amino silicone; chitosans other than the saccharide-based thickeners mentioned previously, and derivatives of these compounds; UV-screening agents; fillers such as nacres, titanium dioxide, resins, or clays; fragrances; peptizers; vitamins; preserving agents; acidic agents; alkaline agents; reducing agents; oxidizing agents; direct dyes, in particular those chosen from cationic and natural direct dyes; oxidation dyes; or a mixture of two or more these compounds.

In embodiments having more than one subformulation, the optional at least one additional component may be in part (A) and/or part (B).

The above additional components may be present in an amount ranging up to about 20% by weight, relative to the total weight of the composition.

Solvent

The compositions according to various embodiments of the disclosure optionally comprise at least one solvent chosen in particular from hydrophilic solvents and hydrophobic solvents. In embodiments having more than one subformulation, the optional at least one solvent may be in part (A) and/or part (B).

Nonlimiting examples of hydrophilic solvents include linear or branched, saturated or unsaturated monoalcohols, comprising from 2 to 10 carbon atoms; or aromatic alcohols.

In some embodiments, the hydrophilic solvent is a linear or branched saturated monoalcohol. In particular, the solvent may be ethyl alcohol, isopropyl alcohol, propyl alcohol, butyl alcohol, or mixtures thereof. According to various embodiments, the solvent is ethyl alcohol, isopropyl alcohol, or a mixture thereof.

In some embodiments, the solvent is phenylethyl alcohol.

According to certain embodiments, the solvent is a single alcohol or a mixture of alcohols.

The total amount of solvent may range from about 0.01% to about 50% by weight, such as from about 1% to about 20% by weight, or from about 5% to about 15% by weight, relative to the total weight of the composition.

Water

The composition that may be used in the process according to the invention advantageously comprises water.

In embodiments having more than one subformulation, water may be in part (A) and/or part (B).

According to various embodiments, the water advantageously represents from 1% to 95%, preferably from 20% to 90%, and more preferentially from 40% to 85%, by weight relative to the total weight of the composition.

Form of Composition

The composition according to the disclosure may be in the form of a wax, a paste, a cream, a gel, a foam, a spray, or a lotion.

According to various embodiments, the composition is in the form of a gel.

In certain embodiments, the composition in the form of a gel has good spreadability and/or adherence to the keratin fibers.

PH of Composition

The composition according to the disclosure may have a pH ranging from about 4 to about 9, such as from about 5 to about 8, from about 6 to about 7, or about 6.5, according to various embodiments.

Methods

Methods of treating hair are also disclosed, said methods comprising applying a composition according to the disclosure onto keratin fibers in order to change the appearance of the keratin fibers. In at least certain embodiments, various methods comprise maintaining curls while obtaining good curl definition and regularity, better movement, and/or good volume, frizz control, and discipline.

In various embodiments, the effect of the treatment may be long lasting. In some embodiments, the resulting effect of the treatment on the hair may remain after at least three shampoos, at least six shampoos, at least eight shampoos, or at least ten shampoos.

The methods according to embodiments of the disclosure comprise applying to the keratin fibers the composition, optionally followed by a heat treatment of the keratin fibers.

Applying the Composition

In a first embodiment of the method according to embodiments of the disclosure, the composition is applied to wet or dry hair, for example clean and dry hair, with or without a leave-on time.

According to some embodiments, the hair is first shampooed, for example with a neutral shampoo.

In various embodiments, the shampooed hair is then dried, for example with a towel or hairdryer. The hair may be thoroughly or completely dried, or the hair may be partially dried.

In some embodiments of the method according to the disclosure, the applying of the composition to the keratin fibers is performed on clean and/or dry keratin fibers, for example curly hair that is clean and dry.

The bath ratio of the applied formulation may range from about 0.1 to about 10, and more particularly from about 0.2 to about 5.

As used herein, the term "bath ratio" means the ratio between the total weight of the applied composition and the total weight of keratin fibers to be treated.

According to some embodiments, when a leave-on time is observed, said leave-on time ranges from about 5 minutes to about 1 hour.

In some embodiments, the keratin fibers are optionally combed. In some embodiments, the combing can serve to remove excess composition from the keratin fibers. The combing may take place before or after the optional leave-on time.

In some embodiments, the composition comprises more than one subformulation. In particular, various embodiments of the composition comprise parts (A) and (B). Part (A) comprises (a) at least one compound chosen from urea and urea derivatives; and part (B) comprises (b) at least one polyol compound. Additional components (c) at least one monoalcohol, and optionally (d) at least one amino silicone may be present in part (A) and/or part (B). According to certain embodiments, water is present in both part (A) and part (B), and at least one thickener is present in either part (A), part (B), or both part (A) and part (B).

The parts (A) and (B) of the composition may be applied separately to the keratin fibers, as a 2-step process, or they may be applied simultaneously, for example when dispensed from a double chamber container and mixed as the composition is applied to the keratin fibers. Alternatively, the parts (A) and (B) of the composition may be mixed prior to application to the keratin fibers, for example at least about 1 minute before application, at least about 5 minutes before application, at least about 15 minutes before application, or at least about 30 minutes before application.

According to certain embodiments, when the composition comprises urea, the composition comprises a first subformulation (A) comprising urea, and a second subformulation (B) comprising at least one polyol compound. The first subformulation (A) and the second subformulation (B) are mixed at the moment of application, or prior to application.

In some embodiments, the composition and/or at least one of the first subformulation and the second subformulation is stable for an extended period of time at various storage temperatures. In certain embodiments, the composition exhibits stability for at least one month, at least three months, at least six months, at least nine months, or at least twelve months, at storage temperatures such as about 4° C., about room temperature, about 25° C., or about 45° C.

Heat Treatment

The heat treatment of the keratin fibers may optionally be performed by a heating tool having a temperature ranging from about 40° C. to about 210° C., such as from about 45° C. to about 200° C., from about 50° C. to about 190° C., from about 80° C. to about 170° C. or from about 100° C. to about 150° C. According to some embodiments, the heating tool is at a temperature lower than about 210° C., such as lower than about 190° C., or lower than about 150° C. In some embodiments, the heating tool is at a temperature of about 149° C. or about 190° C.

In some embodiments, the heat treatment step has a duration ranging from about 5 seconds to about 1 hour, such as from about 5 seconds to about 1 minute, per lock of hair.

This heat treatment step may be performed using at least one heating tool such as a straightening iron, a flat iron, a curling iron, a crimping iron, a waving iron, a hood, a hairdryer, an infrared heating system, or a heating roller.

At least one heating tool is used once or in succession to the keratin fibers, wherein the heating tool is at a temperature ranging from about 40° C. to about 190° C., such as from about 50° C. to about 180° C., or from about 100° C. to about 150° C., for a time ranging from about 5 seconds to about 1 hour and particularly from about 5 seconds to about 1 minute, per lock of hair.

In some embodiments, a hairdryer is used to heat the hair.

According to various embodiments, an iron such as a flat iron, a straightening iron, a crimping iron, or a waving iron is used to heat the hair. In some embodiments, the iron is passed over each lock of hair a maximum of about 5 passes, such as at most 4 passes, at most 3 passes, at most 2 passes, or at most 1 pass. Each pass may be fast, medium, or slow, such as about 10 inches/sec, about 5 inches/sec, about 3 inches/sec, about 2 inches/sec, about 1 inch/sec, or about 0.5 inch/sec. In some embodiments, the speed of each pass with the iron ranges from about 0.5 inch/sec to about 10 inches/sec, such as from about 1 inch/sec to about 5 inches/sec, or about 2 inches/sec to about 4 inches/sec.

In some embodiments, a hairdryer is used to heat the hair, followed by use of a flat iron.

According to certain embodiments, one pass of the flat iron at a temperature of about 149° C. is used per lock of hair.

Post Treatment

The keratin fibers may then optionally undergo at least one of the following processes: rinsing, shampooing, treatment with a rinse-out hair conditioner, and/or drying. In some embodiments, the drying is performed using a hood or a hairdryer.

In some embodiments, the keratin fibers are rinsed with water.

According to various embodiments, the keratin fibers are shampooed, for example with a neutral shampoo, and dried. The drying may be performed with a tool, for example a hairdryer, or by allowing the hair to air dry naturally.

In a second embodiment, the method according to the disclosure is performed at least two times, optionally spaced by at least one cosmetic treatment, in particular spaced by at least one shampoo washes, to treat hair that has regrown or that has undergone other treatments liable to cause changes in the curliness, or to obtain the desired shape or the desired shape intensity.

The methods according to at least certain embodiments of the disclosure do not comprise the application of a reducing composition either before, during, or after the application of the composition.

Embodiments that do not comprise the application of a reducing composition may be less aggressive to the hair than embodiments that do comprise the application of a reducing composition.

Kits

In further embodiments, the disclosure relates to kits containing the compositions according to the disclosure, where parts (A) and (B) are packaged in separate compartments, such as, for example, a dual chamber container optionally with a dispenser.

It to be understood that, as used herein the terms "the," "a," or "an," mean "at least one," and should not be limited to "only one" unless explicitly indicated to the contrary. Thus, for example, reference to "a portion" includes examples having two or more such portions unless the context clearly indicates otherwise.

It should be understood that all patents and published patent applications referenced are incorporated herein in their entireties.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on.

All numbers, amounts, ranges, etc., are intended to be modified by the term "about," whether or not so expressly stated. Similarly, a range given of "about 1% to 10%" is intended to have the term "about" modifying both the 1% and the 10% endpoints.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. For example, the term "about" can mean within 10% of the indicated number (e.g. "about 10%" means 9%-11% and "about 2%" means 1.8%-2.2%), such as within 9%, 8%, 7%, 6%, 5%, 4%, 3%, 2%, or 1%, according to various embodiments.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

It is understood that when an amount of a component is given, it is intended to signify the amount of the active material, unless otherwise indicated.

The compositions and methods according to the present disclosure can comprise, consist of, or consist essentially of the elements and limitations described herein, as well as any additional or optional ingredients, components, or limitations described herein or otherwise known in the art.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

EXAMPLES

The following Examples are provided for illustrative purposes only, and are not intended to be limiting.

In each of the following examples, unless otherwise described or stated, the amounts of components given are in terms of percentage of active material (AM).

Example I

A composition according to Example 1 was prepared by first preparing Part A and Part B according to Table 1 below.

TABLE 1

|  | Example 1 |
|---|---|
| Part A (5% by weight of the total weight of the composition): | |
| Urea | 5 |
| Part B (95% by weight of the total weight of the composition): | |
| Propanediol | 10.004 |
| Amodimethicone | 0.150 |
| Thickener | 0.900 |
| Denatured Alcohol | 9.313 |
| Additonal components (e.g, surfactants, preservatives: Phenoxyethanol, Trideceth-5, Trideceth-10, Glycerin, Acetic Acid) | 0.121 |
| Water | 74.412 |

A mixture of Part A and Part B for Example 1 was applied to a head of clean and dry Type V, sensitized natural hair. The excess composition was removed from the hair with a comb. The hair was dried using a blow dryer. A flat iron at 149° C. was passed over each lock of hair one time. The hair was then shampooed with a neutral shampoo and allowed to dry naturally.

Figure 1B:
FIG. 1B is a photograph showing a head of hair following treatment of Example I.
Figure 1C:
FIG. 1C is a photograph showing a head of hair treated according to Example I after three shampoos.
Figure 1D:
FIG. 1D is a photograph showing a head of hair treated according to Example I after six shampoos.
Figure 8A:
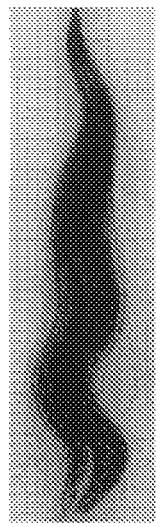
FIGS. 8A-8B are photographs showing the lock of hair following treatment of Example 7, with FIG. 8A showing the lock after treatment of Example 7, and FIG. 8B showing the lock treated according to Example 7 after ten shampoos.
Figure 8B:
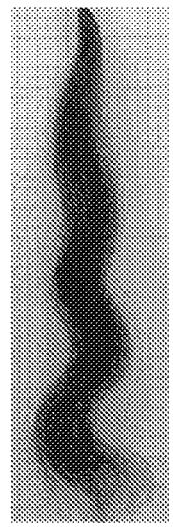

FIGS. 1A-1D show the head of hair before and after the treatment. FIG. 1A is a photograph showing the head of clean and dry hair before the treatment of Example I. FIG. 1B is a photograph showing the head of hair following treatment of Example I. FIG. 1C is a photograph showing the head of hair treated according to Example I after three shampoos. FIG. 1D is a photograph showing the head of hair treated according to Example I after six shampoos.

As shown in FIGS. 1A-1D, hair treated according to Example I exhibited a reduction in both volume and frizz, more shine and discipline, more cosmeticity, and better curl definition. These improvements were long-lasting through six shampoos.

Example II

Examples 2-8 were prepared by first preparing Part A and Part B according to Table 2 below. Example 9 was prepared by first preparing Part A and Part B according to Table 3 below.

TABLE 2

| | Example 2 | Example 3 | Example 4 | Example 5 | Example 6 | Example 7 | Example 8 |
|---|---|---|---|---|---|---|---|
| Part A (5 to 10% by weight of the total weight of the composition):: | | | | | | | |
| Urea | 10 | 10 | 10 | 10 | 5 | 10 | 10 |
| Part B (95 to 90% by weight of the total weight of the composition):: | | | | | | | |
| Butylene Glycol | — | 9.477 | — | — | — | 9.477 | 9.477 |
| Propanediol | 9.477 | — | 9.477 | 9.477 | 10.004 | — | — |
| Additonal components (e.g, surfactants, preservatives: Phenoxyethanol, Trideceth-5, Trideceth-10, Glycerin, Acetic Acid) | 0.115 | 0.115 | 0.115 | 0.115 | 0.121 | 0.115 | 0.115 |
| Amodimethicone | 0.142 | 0.142 | 0.142 | 0.142 | 0.150 | 0.142 | 0.142 |
| Thickener (Hydroxyethyl cellulose, Hydroxypropyl cellulose, Methyl Ethyl hydroxyethyl cellulose, or Steareth-100/PEG-136/HDI copolymer) | 0.948 | 1.895 | 0.948 | 1.895 | 0.900 | 0.948 | 0.948 |
| Denatured Alcohol | 9.477 | 9.477 | 9.477 | 9.477 | 10.0035 | 9.477 | 9.477 |
| Water | 69.841 | 68.894 | 69.841 | 68.894 | 73.722 | 69.841 | 69.841 |

TABLE 3

| | Example 9 |
|---|---|
| Part A (10% by weight of the total weight of the composition):: | |
| Urea | 10 |
| Part B (90% by weight of the total weight of the composition): | |
| Propanediol | 9.477 |
| Additonal components (e.g, amodimethicone, surfactants, preservatives: Phenoxyethanol, Trideceth-5, Trideceth-10, Glycerin, Acetic Acid) | 1.668 |
| thickener | 0.948 |
| Denatured Alcohol | 9.477 |
| Water | 68.431 |

*commercially available under the tradename BELSIL ADM LOG 1 from the supplier Wacker (15% by weight of active material)

A mixture of Part A and Part B for each of Examples 2-9 was applied to a lock of clean and dry Brazilian Type III hair, and the excess was removed from the lock of hair with a comb. The lock of hair was dried using a blow dryer. A flat iron at 149° C. was passed over the lock of hair one time. The lock of hair was then shampooed with a neutral shampoo and allowed to dry naturally.

FIGS. 2-9 show a lock of hair before and after the treatment. FIGS. 2A-2B are photographs showing a lock of clean and dry hair before the treatment of Example II, with FIG. 2A showing the clean and dry lock, and FIG. 2B showing the clean and dry lock after ten shampoos. FIGS. 3A-3B are photographs showing the lock of hair following treatment of Example 2, with FIG. 3A showing the lock after treatment of Example 2, and FIG. 3B showing the lock treated according to Example 2 after ten shampoos. FIGS. 4A-4B are photographs showing the lock of hair following treatment of Example 3, with FIG. 4A showing the lock after treatment of Example 3, and FIG. 4B showing the lock treated according to Example 3 after ten shampoos. FIGS. 5A-5B are photographs showing the lock of hair following treatment of Example 4, with FIG. 5A showing the lock after treatment of Example 4, and FIG. 5B showing the lock treated according to Example 4 after ten shampoos. FIGS. 6A-6B are photographs showing the lock of hair following treatment of Example 5, with FIG. 6A showing the lock after treatment of Example 5, and FIG. 6B showing the lock treated according to Example 5 after ten shampoos. FIGS. 7A-7B are photographs showing the lock of hair following treatment of Example 6, with FIG. 7A showing the lock after treatment of Example 6, and FIG. 7B showing the lock treated according to Example 6 after ten shampoos. FIGS. 8A-8B are photographs showing the lock of hair following treatment of Example 7, with FIG. 8A showing the lock after treatment of Example 7, and FIG. 8B showing the lock treated according to Example 7 after ten shampoos.

Figure 9A:
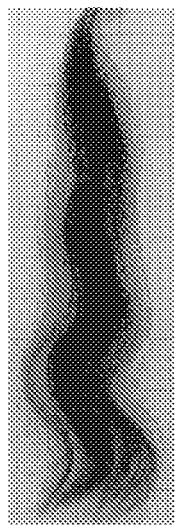
FIGS. 9A-9B are photographs showing the lock of hair following treatment of Example 8, with FIG. 9A showing the lock after treatment of Example 8, and FIG. 9B showing the lock treated according to Example 8 after ten shampoos.
Figure 9B:
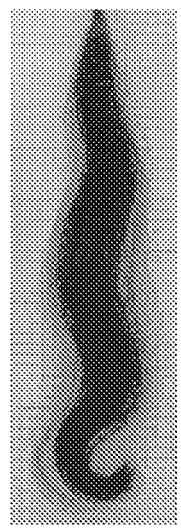

FIGS. 9A-9B are photographs showing the lock of hair following treatment of Example 8, with FIG. 9A showing the lock after treatment of Example 8, and FIG. 9B showing the lock treated according to Example 8 after ten shampoos.

Figure 10A:
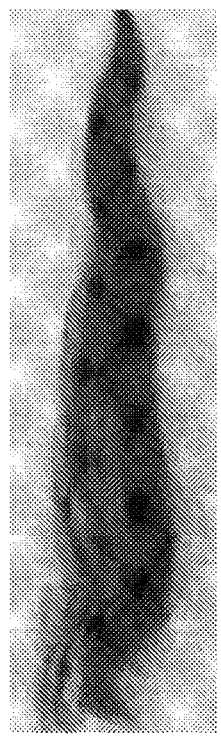
FIGS. 10A-10C show a lock of hair before and after treatment according to Example 9.
Figure 10B:
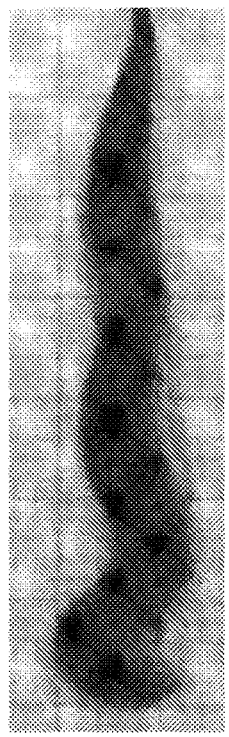
Figure 10C:
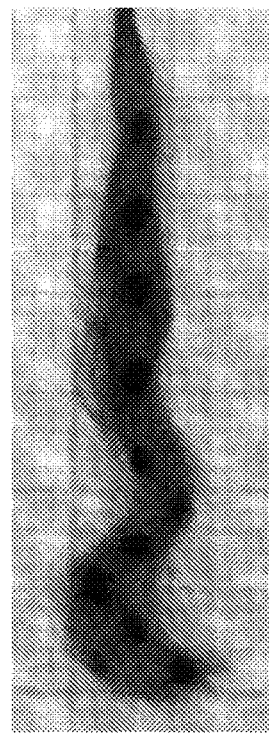

FIGS. 10A-10C show a lock of hair before and after treatment according to Example 9. FIG. 10A is a photograph showing a lock of clean and dry hair before the treatment of Example 9. 10B-10C are photographs showing the lock of hair following treatment of Example 9, with FIG. 10B showing the lock after treatment of Example 9, and FIG. 10C showing the lock treated according to Example 9 after ten shampoos.

As shown in FIGS. 2A-10C, hair treated according to Example II exhibited a reduction in both volume and frizz, more shine and discipline, more cosmeticity, and better curl definition. These improvements were long-lasting through ten shampoos.

Example III

A mixture of Part A and Part B for each of Examples 1-5 and 9 was applied to a respective head of clean and dry Brazilian Type III hair, and the excess was removed from the hair with a comb. The heads of hair were dried using a blow dryer. A flat iron at 149° C. was passed over each lock of hair one time. The heads of hair were then shampooed with a neutral shampoo and allowed to dry naturally.

A panel of experts evaluated the hair treated according to Examples 1-5 and 9. The panel evaluated the hair based on the features of volume reduction, frizz reduction, gain in discipline, gain in curl regularity, and gain in curl definition, both immediately after treatment (IMM) and after ten shampoos (LL). The panel assigned each lock a value of 0-5 for each feature.

Figure 11:
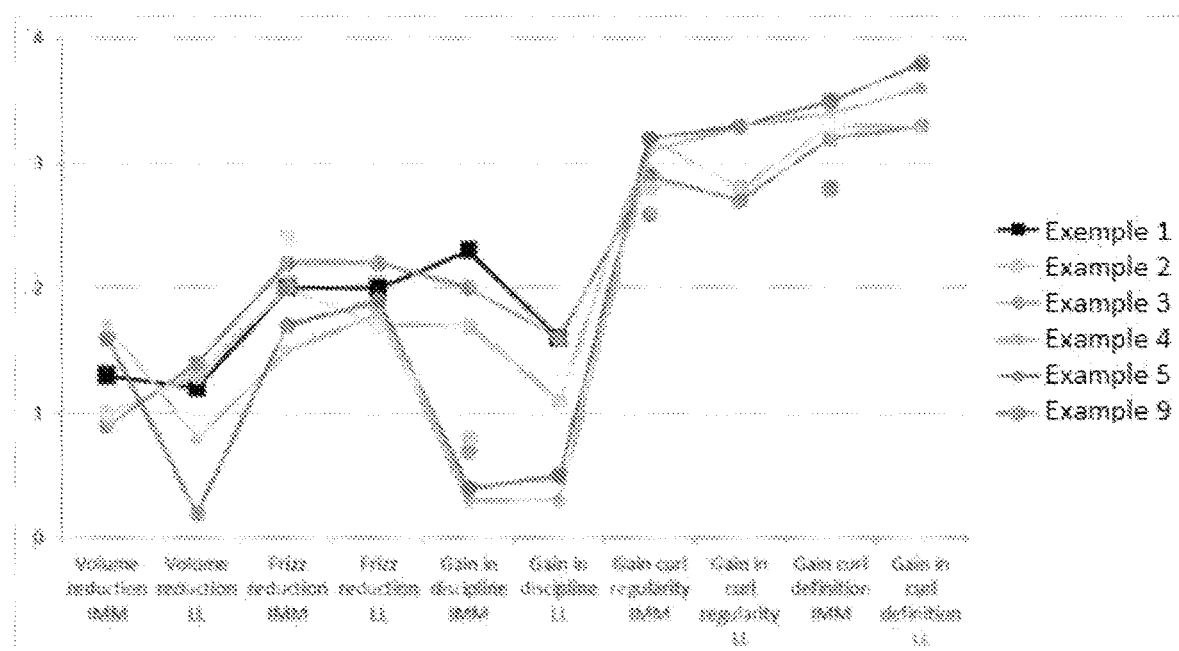
FIG. 11 is a graph showing the results of the evaluation for Examples 1-5 and 9.

FIG. 11 is a graph showing the results of the evaluation for Examples 1-5 and 9.

Example IV

A mixture of Part A and Part B for each of Example 2 and 3 was applied to half a head of clean and dry Type IV, sensitized natural hair. The excess composition was removed from the hair with a comb. The hair was dried using a blow dryer. A flat iron at 149° C. was passed over each lock of hair one time. The hair was then shampooed with a neutral shampoo and allowed to dry naturally.

Figure 12A:
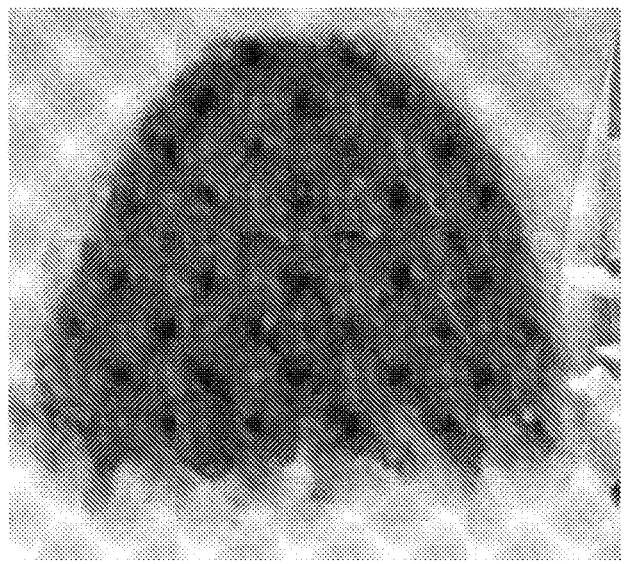
FIGS. 12A-12C show a head of hair before and after treatment with Examples 2 and 3.
Figure 12B:
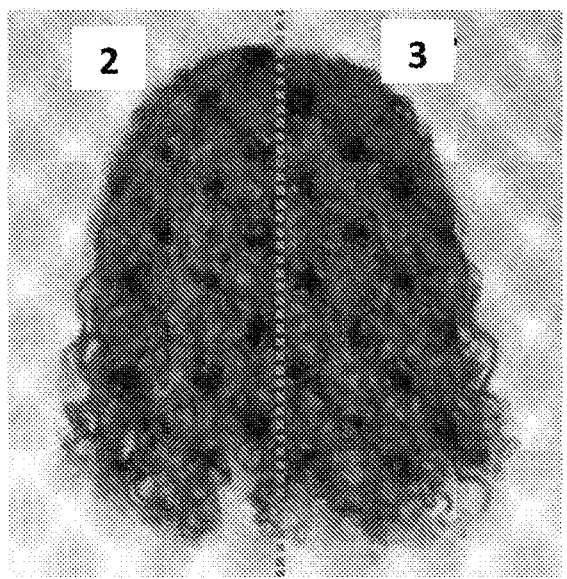
Figure 12C:
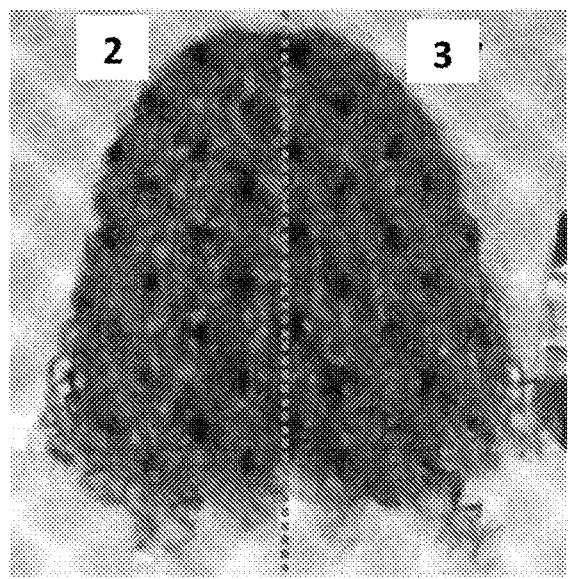
Figure 13A:
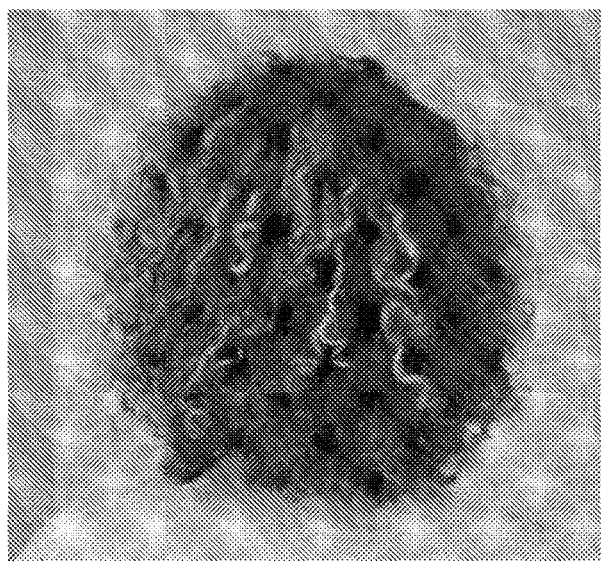
FIGS. 13A-13C show a head of hair before and after treatment with Examples 2 and 3.
Figure 13B:
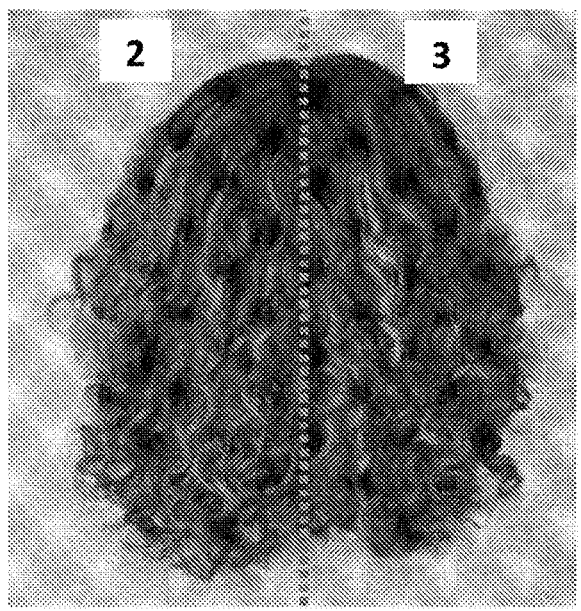
Figure 13C:
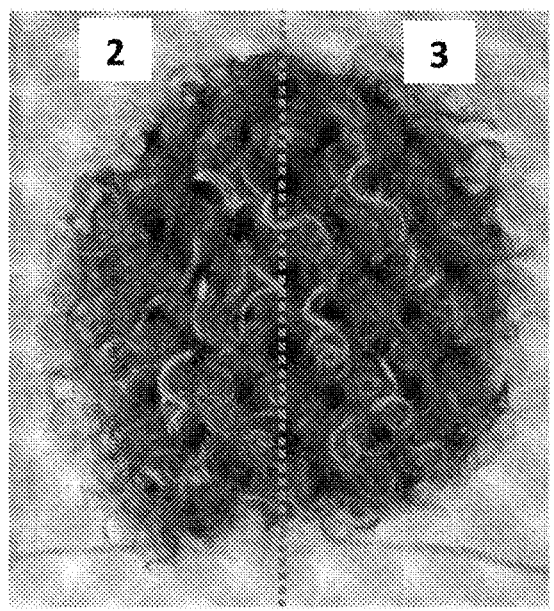

FIGS. 12A-12C and 13A-13C show the heads of hair before and after the treatment. FIGS. 12A and 13A are photographs showing the heads of clean and dry hair before the treatment of Examples 2 and 3. FIGS. 12B and 13B are photographs showing the heads of hair following treatment of Examples 2 and 3. FIGS. 12C and 13C are photographs showing the heads of hair treated according to Examples 2 and 3 after three shampoos.

As shown in FIGS. 12A-13C, hair treated according to Examples 2 and 3 exhibited a reduction in both volume and frizz, more shine and discipline, more cosmeticity, and better curl definition. These improvements were long-lasting through three shampoos.

Example V

Examples 10-13 were prepared by first preparing Part A and Part B according to Table 4 below.

TABLE 4

|  | Example 10 | Example 11 | Example 12 | Example 13 |
|---|---|---|---|---|
| Part A (1 to 5% by weight of the total weight of the composition): | | | | |
| Urea | 1 | 1 | 2.5 | 5 |
| Part B (99 to 95% by weight of the total weight of the composition): | | | | |
| Propanediol | 9.999 | 4.995 | 4.995 | 4.995 |
| Additonal components (e.g., surfactants, preservatives: Phenoxyethanol, Trideceth-5, Trideceth-10, Glycerin, Acetic Acid) | 0.1209 | 0.1209 | 0.1209 | 0.1209 |
| Amodimethicone | 0.150 | 0.150 | 0.150 | 0.150 |
| Thickener | 0.899 | 0.899 | 0.899 | 0.899 |
| Denatured Alcohol | 9.999 | 9.999 | 9.999 | 9.999 |
| Water | 77.732 | 82.736 | 81.236 | 78.736 |

A mixture of Part A and Part B for each of Examples 10-13 was applied to a lock of clean and dry Brazilian Type III hair, and the excess was removed from the lock of hair with a comb. The lock of hair was dried using a blow dryer. A flat iron at 149° C. was passed over the lock of hair one time. The lock of hair was then shampooed with a neutral shampoo and allowed to dry naturally.

Example VI

A mixture of Part A and Part B for Example 1 was applied to a head of clean and dry Type III, sensitized natural hair. The excess composition was removed from the hair with a comb. The hair was dried using a blow dryer. A flat iron at 210° C. was passed over each lock of hair five times. The hair was then shampooed with a neutral shampoo and allowed to dry naturally.

Figure 14A:
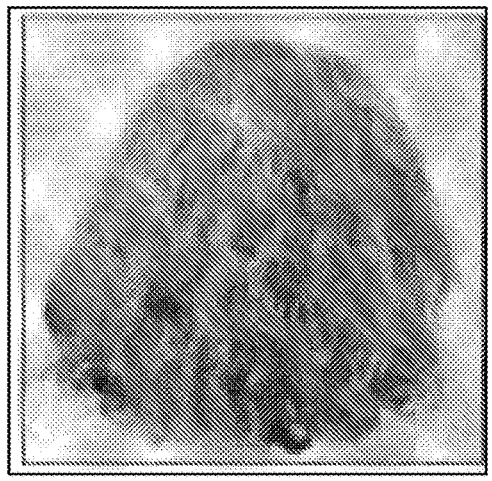
FIGS. 14A-14B show the head of hair before and after the treatment.
Figure 14B:

FIGS. 14A-14B show the head of hair before and after the treatment. FIG. 14A is a photograph showing the head of clean and dry hair before the treatment of Example VI. FIG. 14B is a photograph showing the head of hair following treatment of Example VI.

Figure 15A:
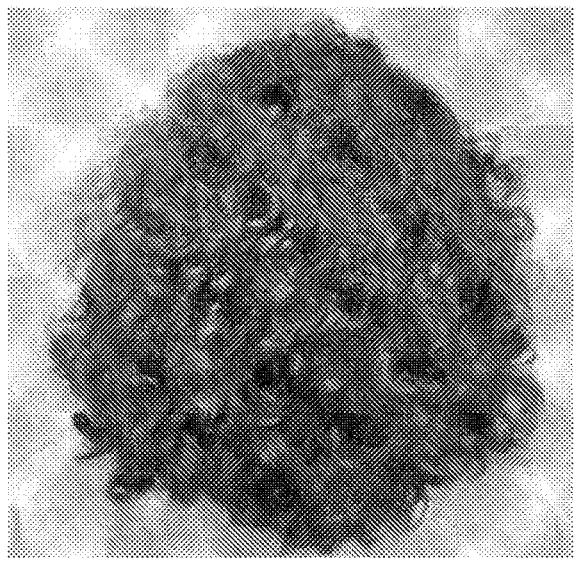
FIGS. 15A-15B show the head of hair before and after the treatment.
Figure 15B:

FIGS. 15A-15B show the head of hair before and after the treatment. FIG. 15A is a photograph showing the head of clean and dry hair before the treatment of Example I, where a mixture of Part A and Part B for Example 1 was applied to a head of clean and dry Type III, slightly damaged natural hair, the excess composition was removed from the hair with a comb, the hair was dried using a blow dryer, and a flat iron at 149° C. was passed over each lock of hair one time. The hair was then shampooed with a neutral shampoo and allowed to dry naturally. FIG. 15B is a photograph showing the head of hair following treatment of Example I.

As shown in FIGS. 14A-15B, hair treated according to Example VI exhibited increased shine and slightly increased discipline, but low straightening and volume reduction, while hair treated according to Example I exhibited volume and frizz reduction, more shine and discipline, more cosmeticity, and better curl definition.

The invention claimed is:

1. A method for improving curl definition of keratin fibers curly hair, said method comprising:
applying to the keratin fibers a composition comprising:
a first part (a) comprising:
(a) at least one compound chosen from urea and urea derivatives; and
a second part (b) comprising:
(b) at least one polyol compound chosen from propylene glycol, butylene glycol, 1,3-propanediol 1,3-butylene glycol, 1,2-pentanediol, dipropylene glycol, hexylene glycol, pentylene glycol, glycerol, ethylene glycol, or mixtures thereof; at least one aminosilicone; and at least one solvent chosen from a monoalcohol; wherein the weight ratio of the total amount of compound chosen from urea and urea derivatives, to the total amount of polyol, ranges from about 0.1 to about 1.5;
and
heating the keratin fibers to a temperature of at least 100° C.;
wherein the method does not include a fixing step.

2. The method of claim 1, wherein the heating is performed using a heating tool chosen from a straightening iron, a flat iron, a curling iron, a crimping iron, a waving iron, a hood, a hairdryer, an infrared heating system, or a heating roller, wherein the heating tool is heated at a temperature of up to about 210° C.

3. The method of claim 1, wherein: the keratin fibers are heated with a flat iron at a temperature of from about 100° C. to about 190° C., and wherein the flat iron is passed over the keratin fibers for one to five passes per lock of keratin fibers.

4. The method of claim 3, wherein: the keratin fibers are heated with a flat iron at a temperature of about 149° C., and wherein the flat iron is passed over the keratin fibers once per lock of keratin fibers.

5. The method of claim 1, wherein: the composition comprises urea, and wherein the first part (a) and the second part (b) are mixed prior to application to the keratin fibers.

6. The method of claim 1, wherein the at least one compound chosen from urea and urea derivative is chosen from urea, methylurea, ethylurea, propylurea, n-butylurea, sec-butylurea, isobutylurea, tert-butylurea, cyclopentylurea, ethoxyurea, hydroxyethylurea, N-(2-hydroxypropyl)urea, N-(3-hydroxypropyl)urea, N-(2-dimethylaminopropyl)urea, N-(3-dimethylaminopropyl)urea, 1-(3-hydroxyphenyl)urea, benzylurea, N-carbamoylmaleamide, N-carbamoylmaleamic acid, piperidinecarboxamide, 1,2,4-triazol-4-ylurea, hydantoic acid, methyl allophanate, ethyl allophanate, acetylurea, hydroxyethyleneurea, 2-(hydroxyethyl)ethyleneurea, diallylurea, chloroethylurea, N,N-dimethylurea, N, N-diethylurea, N, N-dipropylurea, cyclopentyl-1-methylurea, 1,3-dimethylurea, 1,3-diethylurea, 1,3-bis(2-hydroxyethyl)urea, 1,3-bis(2-hydroxypropyl)urea, 1,3-bis(3-hydroxypropyl)urea, 1,3-dipropylurea, ethyl-3-propylurea, sec-butyl-3-methylurea, isobutyl-3-methylurea, cyclopentyl-3-methylurea, N-acetyl-N'-methylurea, trimethylurea, butyl-3,3-dimethylurea, tetramethylurea, parabanic acid, 1,2-dihydro-3H-1,2,4-triazol-2-one, barbituric acid, uracil, 1-methyluracil, 3-methyluracil, 5-methyluracil, 1,3-dimethyluracil, 5-azauracil, 6-azauracil, 5-fluorouracil, 6-fluorouracil, 1,3-dimethyl-5-fluorouracil, 5-aminouracil, 6-aminouracil, 6-amino-1-methyluracil, 6-amino-1,3-dimethyluracil, 4-chlorouracil, 5-chlorouracil, 5,6-dihydrouracil, 5,6-dihydro-5-methyluracil, 2-imidazolidone, 1-methyl-2-imidazolidinone, 1,3-dimethyl-2-imidazolidinone, 4,5-dihydroxyimidazolidin-2-one, 1-(2-hydroxyethyl)-2-imidazolidinone, 1-(2-hydroxypropyl)-2-imidazolidinone, 1-(3-hydroxypropyl)-2-imidazolidinone, 4,5-dihydroxy-1,3-dimethylimidazolidin-2-one, 1,3-bis(2-hydroxyethyl)-2-imidazolidinone, 2-imidazolidone-4-carboxylic acid, 1-(2-aminoethyl)-2-imidazole, 4-methyl-1,2,4-triazoline-3,5-dione, 2,4-dihydroxy-6-methylpyrimidine, 1-amino-4,5-dihydro-1H-tetrazol-5-one, hydantoin, 1-methylhydantoin, 5-methylhydantoin, 5,5-dimethylhydantoin, 5-ethylhydantoin, 5-N-propylhydantoin, 5-ethyl-5-methylhydantoin, 5-hydroxy-5-methylhydantoin, 5-hydroxymethylhydantoin, 1-allylhydantoin, 1-aminohydantoin, hydantoin-5-acetic acid, 4-amino-1,2,4-triazolone-3,5-dione, hexahydro-1,2,4,5-tetrazine-3,6-dione, 5-methyl-1,3,5-triazinon-2-one, 1-methyltetrahydropyrimidin-2-one, 2,4-dioxohexahydro-1,3,5-triazine, urazole, 4-methylurazole, orotic acid, dihydroxyorotic acid, 2,4,5-trihydroxypyrimidine, 2-hydroxy-4-methylpyrimidine, 4,5-diamino-2,6-dihydroxypyrimidine, 1,3-dimethylbarbituric acid, cyanuric acid, 1-methylhexahydropyrimidine-2,4-dione, 1,3-dimethyl-3,4,5,6-tetrahydro-2-(1H)-pyrimidinone, 5-(hydroxymethyl-2,4-(1H,3H)-pyrimidinedione, 2,4-dihydroxypyrimidine-5-carboxylic acid, 6-azathymine, 5-methyl-1,3,5-triazinan-2-one, N-carbamoylmaleamic acid, alloxan monohydrate, or a mixture thereof.

7. The method of claim 1, wherein the total amount of the at least one compound chosen from urea and urea derivatives ranges from about 1% to about 15% by weight, relative to the total weight of the composition.

8. The method of claim 1, wherein the total amount of the at least one polyol ranges from about 1% to about 30% by weight, relative to the total weight of the composition.

9. The method of claim 1, wherein the at least one amino silicone is chosen from:
(a) compounds corresponding to formula (III) below:

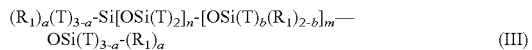

wherein in formula (III):
T is chosen from a hydrogen atom, phenyl, hydroxyl (—OH), $C_1$-$C_8$ alkyl, methyl, $C_1$-$C_8$ alkoxy, or methoxy group,
a is the number 0 or an integer from 1 to about 3,
b is 0 or 1,
m and n are integers such that the sum (n+m) ranges from about 1 to about 2000, n is a number from 0 to about 1999, and m is a number from about 1 to about 2000,
$R_1$ is a monovalent group of formula —$C_qH_{2q}L$ wherein q is an integer from about 2 to about 8 inclusive and L is an optionally quaternized amino group chosen from the following groups:
—N($R_2$)—$CH_2$—$CH_2$—N($R_8$)$_2$,
—N($R_2$)$_2$,
—$N^+$($R_2$)$_3$$Q^-$,
—$N^+$($R_2$)(H)$_2$$Q^-$,
—$N^+$($R_2$)$_2$H$Q^-$,
—N($R_2$)—$CH_2$—$CH_2$—$N^+$($R_2$)(H)$_2$$Q^-$,
wherein $R_2$ is chosen from a hydrogen atom, a phenyl group, a benzyl group, a saturated monovalent hydrocarbon-based group, or a $C_1$-$C_{20}$ alkyl group, and $Q^-$ represents an anionic counterion, a halide ion, fluoride, chloride, bromide, or iodide;

(b) compounds corresponding to formula (VI) below:

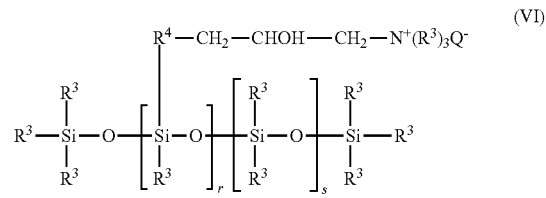

wherein in formula (VI):
$R^3$ is chosen from a monovalent $C_1$-$C_{18}$ hydrocarbon-based group, a $C_1$-$C_{18}$ alkyl group, a $C_2$-$C_{18}$ alkenyl group, or methyl;
$R^4$ is chosen from a divalent hydrocarbon-based group, a $C_1$-$C_{18}$ alkylene group, a divalent $C_1$-$C_{18}$ group, or a $C_1$-$C_8$, alkyleneoxy group;
$Q^-$ represents an anionic counterion chosen from halide ions or chloride;
r represents a mean statistical value from about 2 to about 20;
s represents a mean statistical value from about 20 to about 200 inclusive;

(c) quaternary ammonium silicones or silicones of formula (VII):

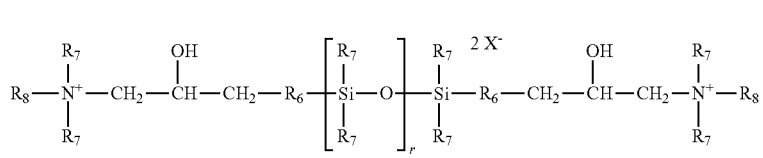

wherein in formula (VII):
$R_6$ is chosen from a divalent hydrocarbon-based group, a $C_1$-$C_{18}$ alkylene group, a divalent $C_1$-$C_{18}$ group, or a $C_1$-$C_8$ alkyleneoxy group linked to the Si atom via a SiC bond;
$R_7$, which may be identical or different, is chosen from a monovalent hydrocarbon-based group containing from 1 to 18 carbon atoms, a $C_1$-$C_{18}$ alkyl group, a $C_2$-$C_{18}$ alkenyl group, a ring comprising 5 or 6 carbon atoms, or methyl;
$R_8$, which may be identical or different, is chosen from a hydrogen atom, a monovalent hydrocarbon-based group containing from 1 to 18 carbon atoms, a $C_1$-$C_{18}$ alkyl group, a $C_2$-$C_{18}$ alkenyl group, or a group -$R_6$-N(H)—C(O)-$R_7$;
$X^-$, which may be identical or different, is chosen from an anionic counterion, a halide ion, chloride, an anionic counterion derived from an organic acid, or ($C_1$-$C_6$)alkylcarboxylate;
r represents a mean statistical value ranging from about 2 to about 200 inclusive;

(d) amino silicones of formula (VIII):

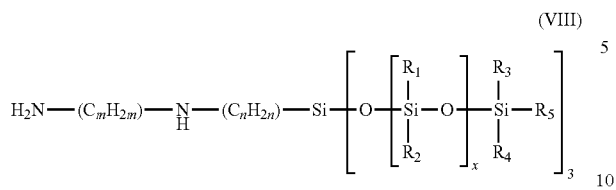

wherein in formula (VIII):
$R_1$, $R_2$, $R_3$ and $R_4$, which may be identical or different, are each chosen from a $C_1$-$C_4$ alkyl group, an aryl group, or a phenyl group,
$R_5$ is chosen from a $C_1$-$C_4$ alkyl group or a hydroxyl group,
n and m, which may be identical or different, represent an integer ranging from about 1 to about 5 inclusive, and
x is such that the amine number ranges from about 0.01 meq/g to about 1 meq/g;

(e) amino silicones bearing polyalkoxylene groups of formula (IX):

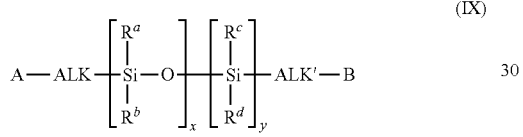

wherein in formula (IX):
$R^a$, $R^b$, $R^c$ and $R^d$, which may be identical or different, are each chosen from a hydroxyl group, a linear or branched $(C_1$-$C_{10})$alkyl group, a $(C_1$-$C_6)$alkyl group, a linear $(C_1$-$C_6)$alkyl group, or methyl;
ALK and ALK', which may be identical or different, represent a linear or branched $(C_1$-$C_{10})$alkylene group, a linear $(C_1$-$C_{10})$alkylene group, or propylene;
A and B, which may be identical or different, represent an aminopolyalkoxy group below:

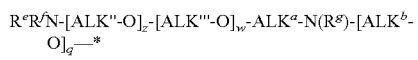

wherein:
\* represents the point of attachment of the aminopolyalkoxy group to the rest of the molecule via ALK or ALK';
$R^e$, $R^f$ and $R^g$, which may be identical or different, are each chosen from a hydrogen atom or a linear or branched $(C_1$-$C_{10})$alkyl group;
ALK" and ALK'", which may be identical or different, are chosen from a linear or branched $(C_1$-$C_{10})$alkylene, a $C_2$ or $C_3$ alkylene group, a divalent group —CH$_2$—CH(CH$_3$)—, or an ethylene group;
ALK$^a$ and ALK$^b$, which may be identical or different, are chosen from a linear or branched $(C_1$-$C_{10})$alkylene, a $C_2$ or $C_3$ alkylene group, an ethylene group, a propylene group, a divalent group —CH$_2$—CH(CH$_3$)—, or a divalent group —CH$_2$—CH(OH)—CH$_2$—;

q, which may be identical or different, represent 0 or 1;
w, which may be identical or different, represent an integer, such that the sum of the w of A and the w of B have a value ranging from about 10 to about 100 inclusive;
z, which may be identical or different, represent an integer, such that the sum of the z of A and the z of B have a value ranging from about 1 to about 20 inclusive;

(f) amino silicones bearing polyalkoxylene groups constituted of polysiloxane blocks and of polyalkoxylene blocks comprising at least one amine group, and amino silicones chosen from:

(1) amino silicones of formula (X):

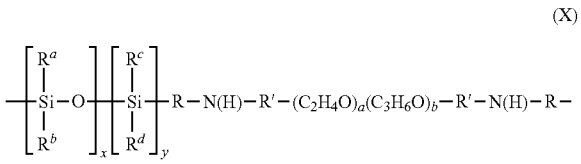

wherein in formula (X):
$R^a$, $R^b$, $R^c$ and $R^d$, which may be identical or different, are chosen from a hydroxyl group, a linear or branched $(C_1$-$C_{10})$ alkyl group, a $(C_1$-$C_4)$alkyl group, a linear $(C_1$-$C_4)$alkyl group, or methyl;
R, which may be identical or different, represent a linear or branched $C_2$-$C_6$ alkylene radical, which is optionally hydroxylated and/or optionally interrupted with an oxygen atom;
a and b, which may be identical or different, represent a number ranging from about 0 to about 100;
R', which may be identical or different, is chosen from a hydrogen atom, a $C_1$-$C_4$ alkyl radical, or a methyl radical;
x denotes an integer ranging from about 1 to about 500 and y denotes an integer ranging from about 1 to about 10;

(2) amino silicones containing units of formula (XI)

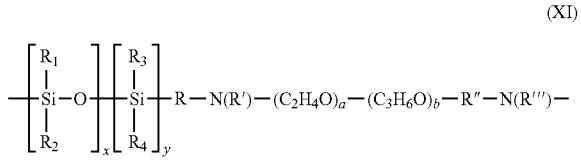

wherein in formula (XI):
$R_1$, $R_2$, $R_3$, and $R_4$, which may be identical or different, are chosen from a $C_1$-$C_4$ alkyl radical or methyl;
R and R", which may be identical or different, represent a linear or branched $C_2$-$C_6$ alkylene radical, which is optionally hydroxylated and/or optionally interrupted with an oxygen atom;
a and b, which may be identical or different, represent an integer ranging from about 0 to about 100;
R' and R'", which may be identical or different, are chosen from a hydrogen atom, a $C_1$-$C_4$ alkyl radical, or a methyl radical; and x is a number ranging from about 1 to about 500 and y is a number ranging from about 1 to about 10;

(3) amino silicones containing units of formula (XII) or of formula (XIII)

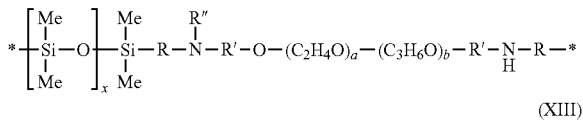

(XII)

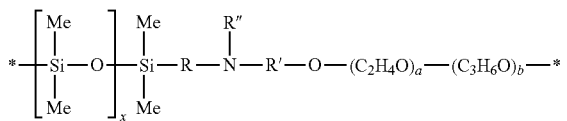

(XIII)

wherein in formulae (XII) and (XIII):
R, which may be identical or different, is chosen from a linear or branched divalent $C_2$-$C_{12}$ alkyl radical, an ethylene radical, a linear or branched propylene radical, a linear or branched butylene radical, or a radical —$CH_2CH_2CH_2OCH(OH)CH_2$—;

R', which may be identical or different, is chosen from a linear or branched divalent $C_2$-$C_{12}$ alkyl radical, an ethylene radical, a linear or branched propylene radical, a linear or branched butylene radical, a radical —$CH_2CH_2CH_2OCH(OH)CH_2$—, or a radical —$CH(CH_3)$—$CH_2$;

R" is chosen from a hydrogen atom or a methyl radical;

x denotes an integer ranging from about 1 to about 10,000;

a represents an integer greater than or equal to 1; and b represents an integer ranging from about 0 to about 200;

or mixtures thereof.

10. The method of claim 1, wherein the at least one amino silicone is amodimethicone.

11. The method of claim 1, wherein the total amount of the amino silicone ranges from about 0.1% to about 4% by weight, relative to the total weight of the composition.

12. The method of claim 1, further comprising at least one thickener.

13. The method of claim 12, wherein the at least one thickener is chosen from hydroxyethylcellulose, steareth-100/PEG-136/HDI copolymer, hydroxypropylcellulose, methylhydroxyethylcellulose, methylethylhydroxyethylcellulose, acrylates/C10-30 alkyl acrylate crosspolymer, hydroxypropylguar, xanthan gum, hydroxypropyl starch phosphate, sodium polyacrylate, polyacrylate crosspolymer-6, or mixtures thereof.

14. The method of claim 12, wherein the total amount of the thickener ranges from about 0.01% to about 10% by weight, relative to the total weight of the composition.

15. The method of claim 1, wherein the total amount of the solvent ranges from about 0.01% to about 50% by weight, relative to the total weight of the composition.

* * * * *